(12) United States Patent
Anton et al.

(10) Patent No.: US 9,249,076 B2
(45) Date of Patent: Feb. 2, 2016

(54) RECYCLABLE EXTRACTANT COMPOSITIONS

(71) Applicants: Douglas Robert Anton, Wilmington, DE (US); Bruce A. Diner, Chadds Ford, PA (US); Steven D. Doig, Wilmington, DE (US)

(72) Inventors: Douglas Robert Anton, Wilmington, DE (US); Bruce A. Diner, Chadds Ford, PA (US); Steven D. Doig, Wilmington, DE (US)

(73) Assignee: BUTAMAX ADVANCED BIOFUELS LLC DE (US)

( * ) Notice: Subject to any disclaimer, the term of this patent is extended or adjusted under 35 U.S.C. 154(b) by 274 days.

(21) Appl. No.: 14/032,328

(22) Filed: Sep. 20, 2013

(65) Prior Publication Data

US 2014/0094630 A1 Apr. 3, 2014

Related U.S. Application Data

(60) Provisional application No. 61/704,300, filed on Sep. 21, 2012.

(51) Int. Cl.
| | |
|---|---|
| *C12P 21/06* | (2006.01) |
| *C12P 7/04* | (2006.01) |
| *C07C 29/86* | (2006.01) |
| *C12P 7/16* | (2006.01) |

(52) U.S. Cl.
CPC . *C07C 29/86* (2013.01); *C12P 7/16* (2013.01); *C12P 21/06* (2013.01); *C12P 7/04* (2013.01); *Y02E 50/10* (2013.01)

(58) Field of Classification Search
CPC .............. C12P 21/06; C12P 7/04; C12P 7/16
USPC .......................................... 435/160, 183, 157
See application file for complete search history.

(56) References Cited

U.S. PATENT DOCUMENTS

| | | | |
|---|---|---|---|
| 3,536,662 A | 10/1970 | Bevilacqua et al. | |
| 4,744,881 A | 5/1988 | Reid | |
| 5,231,017 A | 7/1993 | Lantero et al. | |
| 5,514,583 A | 5/1996 | Picataggio et al. | |
| 5,712,133 A | 1/1998 | Picataggio et al. | |
| 6,703,227 B2 | 3/2004 | Jakel et al. | |
| 7,223,575 B2 | 5/2007 | Zhang et al. | |
| 7,741,119 B2 | 6/2010 | Viitanen et al. | |
| 7,851,188 B2 * | 12/2010 | Donaldson ........... | C12N 9/0006 435/157 |
| 7,993,889 B1 * | 8/2011 | Donaldson ........... | C12N 9/0006 435/157 |
| 8,178,328 B2 | 5/2012 | Donaldson et al. | |
| 8,206,970 B2 * | 6/2012 | Eliot .................... | C12N 9/0006 435/183 |
| 8,373,008 B2 | 2/2013 | Grady et al. | |
| 8,373,009 B2 | 2/2013 | Grady et al. | |
| 8,409,834 B2 | 4/2013 | Burlew et al. | |
| 8,426,173 B2 | 4/2013 | Bramucci et al. | |
| 8,426,174 B2 | 4/2013 | Bramucci et al. | |
| 8,460,439 B2 | 6/2013 | Parten | |
| 8,476,047 B2 | 7/2013 | Burlew et al. | |
| 8,557,540 B2 | 10/2013 | Burlew et al. | |
| 8,563,788 B2 | 10/2013 | Grady et al. | |
| 8,569,552 B2 | 10/2013 | Grady et al. | |
| 8,574,406 B2 | 11/2013 | Grady et al. | |
| 8,617,861 B2 | 12/2013 | Grady et al. | |
| 8,628,643 B2 | 1/2014 | Grady et al. | |
| 8,697,404 B2 | 4/2014 | Anton et al. | |
| 8,759,044 B2 | 6/2014 | Dicosimo et al. | |
| 8,765,425 B2 | 7/2014 | Dicosimo et al. | |
| 8,828,695 B2 | 9/2014 | Grady et al. | |
| 8,865,443 B2 | 10/2014 | Burlew et al. | |
| 8,906,204 B2 | 12/2014 | Xu | |
| 8,968,522 B2 | 3/2015 | Xu et al. | |
| 8,968,523 B2 | 3/2015 | Xu et al. | |
| 8,969,055 B2 | 3/2015 | Grady et al. | |
| 9,012,190 B2 | 4/2015 | Dauner et al. | |
| 9,040,263 B2 | 5/2015 | Anton et al. | |
| 2007/0031918 A1 | 2/2007 | Dunson et al. | |
| 2007/0292927 A1 | 12/2007 | Donaldson et al. | |
| 2008/0182308 A1 | 7/2008 | Donaldson et al. | |
| 2008/0274525 A1 | 11/2008 | Bramucci et al. | |
| 2008/0274526 A1 | 11/2008 | Bramucci et al. | |
| 2009/0203099 A1 | 8/2009 | Caimi et al. | |
| 2009/0246846 A1 | 10/2009 | Viitanen et al. | |
| 2009/0305363 A1 | 12/2009 | Anthony et al. | |
| 2009/0305370 A1 | 12/2009 | Grady et al. | |
| 2010/0143995 A1 | 6/2010 | Erdner-Tindall et al. | |

(Continued)

OTHER PUBLICATIONS

International Search Report and Written Opinion, mailed on Mar. 3, 2014, in International Patent Application No. PCT/US2013/060858.

(Continued)

*Primary Examiner* — Elvis O Price

(57) ABSTRACT

Provided herein are processes comprising providing a fermentation medium comprising a fermentable carbon source, a recombinant microorganism comprising an engineered butanol biosynthetic pathway, and butanol; contacting said fermentation medium with an extractant composition comprising an effective amount of antioxidant or antioxidant-like compound, whereby at least a portion of the butanol in the fermentation medium partitions into the extractant; recovering at least a portion of the butanol and extractant composition from the fermentation medium; recycling the extractant composition recovered in (c) one or more times in the fermentation medium; optionally adjusting the effective amount of antioxidant or antioxidant-like compound in the extractant composition, whereby the rate of oxidation or effect of oxidized products in the recycled extractant composition is substantially reduced and/or avoided such that the extractant composition may be recycled.

22 Claims, 8 Drawing Sheets

(56) References Cited

U.S. PATENT DOCUMENTS

| | | |
|---|---|---|
| 2011/0014670 A1 | 1/2011 | Caimi et al. |
| 2011/0097773 A1 | 4/2011 | Grady et al. |
| 2011/0111472 A1 | 5/2011 | Donaldson et al. |
| 2011/0136193 A1 | 6/2011 | Grady et al. |
| 2011/0250610 A1 | 10/2011 | Liao et al. |
| 2011/0294179 A1 | 12/2011 | Grady et al. |
| 2011/0312044 A1 | 12/2011 | Anton et al. |
| 2011/0312053 A1 | 12/2011 | Burlew et al. |
| 2011/0313206 A1 | 12/2011 | Donaldson et al. |
| 2012/0156738 A1 | 6/2012 | Anton et al. |
| 2013/0164795 A1 | 6/2013 | Lowe et al. |
| 2013/0217060 A1 | 8/2013 | Bramucci et al. |
| 2013/0224728 A1 | 8/2013 | Bramucci et al. |
| 2013/0252297 A1 | 9/2013 | Parten |
| 2013/0295661 A1 | 11/2013 | Roesch et al. |
| 2013/0309738 A1 | 11/2013 | Barr et al. |
| 2014/0018581 A1 | 1/2014 | Grady et al. |
| 2014/0024064 A1 | 1/2014 | Burlew et al. |
| 2014/0073021 A1 | 3/2014 | Bazzana et al. |
| 2014/0073820 A1 | 3/2014 | Bazzana et al. |
| 2014/0093931 A1 | 4/2014 | Dauner et al. |
| 2014/0094630 A1 | 4/2014 | Anton et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | Dicosimo et al. |
| 2014/0178529 A1 | 6/2014 | Anton et al. |
| 2014/0234929 A1 | 8/2014 | Barr et al. |
| 2014/0256020 A1 | 9/2014 | Dicosimo et al. |
| 2014/0273127 A1 | 9/2014 | Fuchs et al. |
| 2014/0273130 A1 | 9/2014 | Anthony et al. |
| 2014/0303408 A1 | 10/2014 | Zaher |
| 2014/0311889 A1 | 10/2014 | Zaher et al. |
| 2014/0363865 A1 | 12/2014 | Burlew et al. |
| 2015/0010975 A1 | 1/2015 | Burlew et al. |
| 2015/0010984 A1 | 1/2015 | Bhalla et al. |
| 2015/0060259 A1 | 3/2015 | Xu et al. |

OTHER PUBLICATIONS

Thaddeus Ezeji et al., "Achievements and perspectives to overcome the poor solvent resistance in acetone and butanol-producing microorganisms," Applied Microbio. Biotechnol. 85(6):1697-1712 (2009).

Lynd et al., "Microbial cellulose utilization: fundamentals and biotechnology," Microbiol. Mol. Biol. Rev. 66:506-77 (2002).

Fung et al., "Effect of phenolic antioxidants on microbial growth," CRC Critical Reviews Microbiol. 12(2):153-83 (1985).

Sankaran, "Comparative antimicrobial action of certain antioxidants and preservatives," J. Food Science Technol. 13:203-4 (1976).

Yankah et al., "Quantitative determination of butylated hydroxyanisole, butylate hydroxytoulene, and tert-butyl hydroquinone in oils, foods, and biological fluids by high-performance liquid chromatography with fluorometric detection," Lipids AOC Press 33(11):1139-45 (1998).

Piddocke et al., "Revealing the beneficial effect of protease supplementation to high gravity beer fermentations using"—omics "techniques," Microbial Cell Factories 10:27 (2011).

Ohta et al., "Genetic Improvement of Escherichia coli for ethanol production: chromosomal integration of Zymomonas mobilis genes encoding pyruvate decarboxylase and alcohol dehydrogenase II," Appl. Enivron. Microbiol. 57:893-900 (1991).

Underwood et al., "Flux through citrate synthase limits the growth of ethanologenic Escherichia coli KO11 during xylose fermentaiton," Appl. Environ. Microbiol. 68:1071-81 (2002).

Shen and Liao, "Metabolic engineering of Escherichia coli for 1-butanol and 1-propanol production via the keto-acid pathways," Metab. Eng. 10:312-20 (2008).

Hanai et al., "Engineered synthetic pathway for isopropanol production in Escherichia coli," Appl. Environ. Microbiol. 73:7814-8 (2007).

Feldman et al., "Pentose metabolism in Zymomonas mobilis wild-type and recombinant strains," Appl. Microbiol. Biotechnol. 38:354-61 (1992).

Zhang et al., "Metabolic engineering of a pentose metabolism pathway in ethanologenic zymomonas mobilis," Science 267:240-3 (1995).

Durre, "New insights and novel developments in clostridial acetone/butanol/isopropanol fermentation" Appl. Microbiol. Biotechnol. 49:639-48 (1998).

Groot et al., "Technologies for Butanol recovery integrated with fermentations," Process Biochem. 27:61-75 (1992).

Guo et al., "Pervaporation study on the dehydration of aqueous butanol solutions: a comparison of flux vs. permeance, separation factor vs. selectivity," J. Membrane Sci. 245:199-210 (2004).

Trotter et al., "Old yellow enzymes protect against acrolein toxicity in the yeast Saccharomyces cerevisiae," Appl. Environ Microbiol. 72:4885-92 (2006).

Berlett and Stadtman, "Protein oxidation in aging, disease, and oxidative stress," J. Biol. Chem. 272:20313-6 (1997).

Robert and Penaranda, , "Studies on aldehyde-protein interactions. I. Reaction of Amino Acids with lower aldehydes," J. Polymer Sci. 12:337-50 (1954).

Sherwin, "Oxidation and antioxidants in fat and oil processing," J. Am. Oil. Chem. Soc. 55:809-14 (1978).

Sherwin, "Antioxidants for vegetable oils," J. Am. Oil Chem. Soc. 53:430-6 (1976).

Ishii et al., "Production of butanol by Clostridium acetobutylicum in extractive fermentation system," J. Chem. Engineering of Japan 18:125-30 (1985).

Bellion et al., Microb. Growth C1 Compd. [Int. Symp.] 7th (1993), 415-32, Editor(s): Murrell, J. Collin; Kelly, Don P. Publisher: Intercept, Andover, UK.

Sulter et al., "Proliferation and metabolic significance of peroxisomes in Candida boidinii during growth on D-alanine or oleic acid as the sole carbon source," Arch. Microbiol. 153:485-9 (1990).

\* cited by examiner

RECYCLABLE EXTRACTANT COMPOSITIONS

CROSS REFERENCE TO RELATED APPLICATION

This application claims benefit of priority from U.S. Provisional Application No. 61/704,300, filed Sep. 21, 2012, which is hereby incorporated by reference in its entirety.

FIELD OF INVENTION

The present invention relates to processes for recovering butanol produced in a fermentative process using an extractant. More specifically, the invention relates to maintaining extractant efficiency over time including over extractant recycles by, for example, providing a sufficient amount of antioxidants or antioxidant-like compounds with the extractant.

BACKGROUND

Butanol is an important industrial chemical with a variety of applications, including use as a fuel additive, as a feedstock chemical in the plastics industry, and as a food-grade extractant in the food and flavor industry. Accordingly, there is a high demand for butanol, as well as for efficient and environmentally friendly production methods. One such environmentally friendly production method includes the production of butanol utilizing fermentation by microorganisms. During the fermentation process, butanol can be extracted from the fermentation medium using an extractant.

The use of fatty acids as an extractant for recovering butanol from a fermentation process is attractive as fresh fatty acid can be constantly generated by lipase-catalyzed hydrolysis of available corn oil, introduced with the corn mash. The ratio of linoleic:oleic:palmitic acid in corn oil triglycerides is approximately 4:2:1 on a weight basis. Given the high concentration of polyunsaturated fatty acids, the risk of oxidation is high if the polyunsaturated fatty acids are allowed contact with oxygen, which may occur during fermentation and/or during other steps of the process for producing butanol. Antioxidants, particularly the tocopherols, associated with raw corn oil provide some protection. However, given that the fatty acids generated from the corn oil can be reused and recycled to extract fermentative products such as butanol many times and the fact that the antioxidant is consumed when it interrupts the oxidation cycle, a sufficient amount of antioxidants or antioxidant-like compounds in the extractant is needed to keep the rate of oxidation at an acceptably low level or to counteract the effect of oxidation products (e.g., aldehydes and ketones), particularly when the fermentation process is carried out under aerobic and/or microaerobic conditions.

The present invention satisfies the need to maintain or provide an effective level of antioxidants or antioxidant-like compounds in an extractant for recovering butanol from a fermentation process.

BRIEF SUMMARY OF THE INVENTION

Provided herein are methods for improving extraction of product alcohols produced by fermentation of renewable resources (i.e., biomass) using recombinant microorganisms. Specifically, provided herein are methods for improving extraction of butanol produced by fermentation of biomass using recombinant microorganisms engineered with a butanol biosynthetic pathway. Such improvements include controlling the rate of oxidation or the effect of oxidation products on an extractant comprising unsaturated fatty acids. Provided herein are processes for maintaining or providing an effective amount of antioxidant or antioxidant-like compound in an extractant to recover butanol from a fermentation process. The processes comprise (a) providing a fermentation medium comprising a fermentable carbon source, a recombinant microorganism comprising an engineered butanol biosynthetic pathway, and butanol; (b) contacting said fermentation medium with an extractant composition comprising an effective amount of antioxidant or antioxidant-like compound, whereby at least a portion of the butanol in the fermentation medium partitions into the extractant; (c) recovering at least a portion of the butanol and extractant composition from the fermentation medium; (d) recycling the extractant composition recovered in (c) one or more times to the fermentation medium; and (e) optionally adjusting the effective amount of the antioxidant or antioxidant-like compound in the recycled extractant composition, whereby the rate of oxidation or the effect of oxidation products in the recycled extractant composition is substantially reduced and/or avoided such that the extractant composition may be recycled as provided in step (d) for at least ten recycles. Optionally, the extractant composition can be recycled for at least twenty recycles. Optionally, the extractant composition may be recycled for at least fifty recycles.

Adjusting the effective amount of antioxidant or antioxidant-like compound of the extractant composition can, for example, comprise supplementing the recycled extractant composition with one or more antioxidants or antioxidant-like compounds. Supplementation may occur through addition of antioxidant or antioxidant-like compound to the extractant composition prior to addition to the fermentation vessel, during fermentation, or with extractant recycle. Supplementation may also occur by providing antioxidant or antioxidant-like compound with the biomass (e.g., corn mash), with fermentation medium, or produced by the recombinant microorganism engineered to produce butanol. In an embodiment, the feedstock (i.e., biomass) which is used as the carbon source for fermentation of butanol may be selected based on having an improved fatty acid profile and/or natural antioxidant or antioxidant-like composition, or may be genetically modified to provide a fatty acid profile that is less susceptible to oxidation or that includes an effective amount of antioxidant or antioxidant-like compound for improved extraction of butanol during fermentation.

During production of butanol in which butanol is recovered by extraction, extractant recycle may be accomplished through various means, including distillation of extractant and butanol. Recycling the extractant composition is facilitated by preventing or reducing the rate of oxidation of the extractant or the effect of oxidation products on the extractant that may be exposed to oxygen during recovery and/or other processing in butanol production. The extractant composition can be adjusted at each recycle of the extractant composition to maintain an effective level of antioxidants or antioxidant-like compounds. Alternatively, the extractant composition can be adjusted once such that it comprises an effective amount of antioxidant or antioxidant-like compound for at least 5 recycles, preferably 10 recycles, more preferably 20 recycles, most preferably 100 recycles. Alternatively, the extractant composition can be adjusted every other recycle. A person skilled in the art will be capable of determining at which recycle number a given extractant composition will need to be adjusted, which may include monitoring the oxidative state of the extractant composition. Determining the oxidation state of the extractant composition may be accomplished by monitoring the loss of one or more components of the extractant (e.g., the loss of linoleic 18:2 in corn oil fatty acid (COFA)). Optionally, determining the oxidation state of the extractant composition may be accomplished by monitoring the antioxidative activity index of the extractant (e.g., by use of the Rancimat method). Optionally, determining the oxidation state of the extractant composition may be accomplished by monitoring one or more indicators of fermentation productivity, such as rate, titer, yield of product alcohol, in addition to measuring the growth rate or effective yield of a recombinant microorganism in the fermentation process. Determining the oxidation state of the extractant can be done at each recycle, every other recycle, every third recycle, every fourth recycle, every fifth recycle, every tenth recycle, or every twentieth recycle. A person skilled in the art will be capable of determining at which recycle number the oxidation state will need to be monitored.

Supplementing the extractant composition with one or more antioxidants or antioxidant-like compounds may also comprise addition of a fresh or unused portion of the extractant composition comprising an effective amount of antioxidant or antioxidant-like compound to the recycled extractant composition. Optionally, supplementing the recycled extractant with one or more antioxidants or antioxidant-like compounds can comprise the addition of the antioxidant or antioxidant-like compound directly to the recycled extractant composition to form an extractant composition comprising an effective amount of antioxidant or antioxidant-like compound.

Antioxidants may be selected from, but are not limited to, the group consisting of tocopherols, tocotrienols, amino acids with antioxidant activity, butylated hydroxyanisole (BHA), butylated hydroxytoluene (BHT), other alkylated phenols, epigallocatechin gallate (EGCG), epigallocatechin (EGC), epicatechin gallate (ECG), gallic acid, gallic esters (e.g., propyl gallate), carnosol, carnosic acid, ursolic acid, tanshen I, dihydrotanshinone, tanshinone IIA, tanshinone IIB, danshenxinkun B, peroxidase enzymes, immobilized borohydrides, L-ascorbic acid 6-palmitate, anthocyanidins, anthocyanins, ethoxyquin, tertiary-butylhydroquinone (TBHQ), and combinations thereof. In certain embodiments, the one or more antioxidants can comprise tocopherols. In certain embodiments, the one or more antioxidants can comprise BHT. In certain embodiments, the one or more antioxidants can comprise BHT and BHA.

Optionally, the one or more antioxidants or antioxidant-like compounds can comprise amino acids. Amino acids with antioxidant activity can include, but are not limited to, cysteine, methionine, phenylalanine, histidine, tryptophan, and tyrosine. Amino acids with antioxidant activity can be added to the recycled extractant composition with a fresh or unused portion of the extractant composition. Optionally, in a fermentation process, the fermentable carbon source can be provided by processing biomass. In such instances, amino acids can be added to the recycled extractant composition by further processing the biomass with the addition of enzymes or other agents which produce antioxidant and antioxidant-like compound from biomass. Optionally, a protease is added to the biomass, whereby the protease releases free amino acids from the biomass which provide antioxidant or antioxidant-like activity for the extractant composition.

The protease can, for example, be deactivated at a temperature of at least about 85° C. Deactivation of the protease can take at least 15 minutes at a temperature of at least about 85° C. Methods to deactivate proteases are known in the art. Optionally, the protease is a universal protease capable of hydrolyzing all amino acid bonds in a polypeptide.

In certain embodiments, an effective amount of antioxidant or antioxidant-like compound can be indicated by measuring the rate of loss of oxidation sensitive components of the extractant (e.g., the loss of the linoleic 18:2 in corn oil fatty acid (COFA)) relative to the loss of those components in a sample of extractant that does not contain an antioxidant or antioxidant-like compound. An extractant composition with an effective amount of antioxidant or antioxidant-like compound is indicated where the rate of loss of oxidation sensitive components relative to the rate of loss of oxidation sensitive components in an extractant without antioxidants or antioxidant-like compounds is less than about 0.9, preferably the ratio is less than about 0.5, more preferably the ratio is less than about 0.2, and most preferably the ratio is less than about 0.1. The rate can be determined by determining the amount of each component of the extractant (e.g., the amount of linoleic 18:2) before and after each recycle. Analytical GC using AOCS method Ce 1e-91 combined with AOCS method Ce2-66 or similar methods can be used to determine the amounts of each component with fatty acid and fatty ester based extractants, but other techniques would be apparent to one skilled in the art.

Optionally, an extractant composition comprising an effective amount of antioxidant has an antioxidant activity index of at least about 1.1. The antioxidative activity index of the extractant composition may be at least about 1.1 to about 15, at least about 2 to about 12, or at least about 5 to about 10. The antioxidative activity index of the extractant composition may be about 1.1, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15.

Optionally, an effective amount of antioxidant or antioxidant-like compound can be indicated by measuring the peroxide, aldehyde, and/or ketone content of the extractant after each recycle of the extractant and comparing to the measurement of the previous recycle to determine whether there was an increase in peroxide, aldehyde, and/or ketone content of the extractant. An increase in the peroxide, aldehyde, and/or ketone content indicates a diminished level of antioxidant or antioxidant-like compound in the extractant. The levels of the peroxide, aldehyde, and/or ketone content can be determined every recycle of extractant, every other recycle, every fifth recycle, every tenth recycle, or every twentieth recycle. A person skilled in the art will be capable of determining when to measure the peroxide, aldehyde, and/or ketone content of the extractant.

Optionally, the extractant is selected from, but not limited to, the group consisting of corn oil fatty acid (COFA), soy oil fatty acid (SOFA), castor oil fatty acid, oleyl alcohol, COFA based fatty acid methyl esters (FAME), SOFA based FAME, fatty acid butyl esters (FABE), and mixtures thereof.

Also provided are processes for introducing an effective amount of antioxidant or antioxidant-like compound into an extractant composition used to recover butanol from a fermentation process. The processes comprise (a) providing a fermentation medium comprising a fermentable carbon source, a recombinant microorganism comprising an engineered butanol biosynthetic pathway, and butanol, wherein the fermentable carbon source is provided by processing biomass; (b) contacting said fermentation medium with an extractant composition, whereby the extractant composition does not comprise an effective amount of antioxidant or antioxidant-like compound, and whereby at least a portion of the butanol in the fermentation medium partitions into the extractant; (c) adjusting the amount of antioxidant or antioxidant-like compound in the extractant composition by further processing the biomass with a protease, whereby the protease stimulates the release of free amino acids from the biomass and whereby the amino acids provide the extractant composition with an effective amount of antioxidant or antioxidant-like compound; (d) recovering at least a portion of the butanol and extractant composition from the fermentation medium; (e) recycling the extractant composition recovered in (d) one or more times to the fermentation medium; and (f) optionally adjusting the effective amount of antioxidant or antioxidant-like compound in the extractant composition whereby the rate of oxidation or the effect of the oxidation products in the recycled extractant composition is substantially reduced and/or avoided such that the extractant composition may be recycled. Further, the extractant composition may be recycled as provided in step (e) for at least ten recycles. Optionally, the extractant composition may be recycled for at least twenty recycles. Optionally, the extractant composition may be recycled for at least fifty recycles.

Also provided are processes for preventing or reducing the oxidation rate of a recycled extractant or the effect of oxidation products on a recycled extractant. The processes comprise (a) providing a fermentation medium comprising a fermentable carbon source, a recombinant microorganism comprising an engineered butanol biosynthetic pathway, and butanol; (b) contacting said fermentation medium with an extractant composition comprising an effective amount of antioxidant or antioxidant-like compound, whereby at least a portion of the butanol in the fermentation medium partitions into the extractant; (c) recovering at least a portion of the butanol and extractant composition from the fermentation medium; (d) adding antioxidants or antioxidant-like compounds to the extractant composition recovered in (c); and (e) recycling the extractant composition of step (d) one or more times in the fermentation medium.

Also provided are methods for maintaining the oxidative state of an extractant composition during a butanol fermentation process. The methods comprise (a) providing a fermentation medium comprising a fermentable carbon source, a recombinant microorganism comprising an engineered butanol biosynthetic pathway, and butanol; (b) contacting said fermentation medium with an extractant composition comprising an effective amount of antioxidant or antioxidant-like compound, whereby at least a portion of the butanol in the fermentation medium partitions into the extractant; (c) recovering at least a portion of the butanol and extractant composition from the fermentation medium; (d) monitoring one or more of the antioxidative activity index, effective rate, titer, yield of butanol production or the growth of the recombinant microorganism during fermentation; (e) supplementing the extractant composition with antioxidant or antioxidant-like compound following step (d) when said monitoring indicates a decrease in the antioxidative activity index or said monitoring indicates a toxicity to the recombinant microorganism.

Also provided are methods for optimizing extraction of butanol from a butanol fermentation process. The methods comprise (a) providing a fermentation medium comprising a fermentable carbon source, a recombinant microorganism comprising an engineered butanol biosynthetic pathway, and butanol; (b) providing an extractant composition comprising an effective amount of antioxidant or antioxidant-like compound, butanol and free fatty acids, wherein the antioxidant or antioxidant-like compound is produced by the recombinant microorganism during fermentation; and (c) contacting the fermentation medium of (a) with the extractant composition of (b) whereby the butanol partitions into the extractant composition and is distilled from the extractant. Optionally, the methods further comprise recycling the extractant composition of (c) after the butanol is distilled.

Also provided are methods for improving the yield of isobutanol produced during an isobutanol fermentation. The methods comprise (a) providing a fermentation medium comprising a fermentable carbon source, a recombinant microorganism comprising an engineered isobutanol biosynthetic pathway, and isobutanol; (b) providing an extractant composition comprising an effective amount of antioxidant or antioxidant-like compound, isobutanol and free fatty acids; and (c) contacting the fermentation medium of (a) with the extractant composition of (b) whereby isobutanol partitions into the extractant composition, wherein the yield of isobutanol is improved as compared to yield of isobutanol in the absence of the antioxidant or antioxidant-like compound.

Also provided are methods for improving the titer of isobutanol produced during an isobutanol fermentation process. The methods comprise (a) providing a fermentation medium comprising a fermentable carbon source, a recombinant microorganism comprising an engineered isobutanol biosynthetic pathway, and isobutanol; (b) providing an extractant composition comprising an effective amount of antioxidant or antioxidant-like compound, isobutanol and free fatty acids; and (c) contacting the fermentation medium of (a) with the extractant composition of (b) whereby isobutanol partitions into the extractant composition, wherein the titer of isobutanol production is improved as compared to titer of isobutanol production in the absence of the antioxidant or antioxidant-like compound.

Also provided are methods for improving the rate of an isobutanol production during an isobutanol fermentation process. The methods comprise (a) providing a fermentation medium comprising a fermentable carbon source, a recombinant microorganism comprising an engineered isobutanol biosynthetic pathway, and isobutanol; (b) providing an extractant composition comprising an effective amount of antioxidant or antioxidant-like compound, isobutanol and free fatty acids; and (c) contacting the fermentation medium of (a) with the extractant composition of (b) whereby the isobutanol partitions into the extractant composition, wherein the rate of isobutanol production is improved as compared to rate of isobutanol production in the absence of the antioxidant or antioxidant-like compound.

Also provided are methods for increasing the levels of butanol partitioning into an extractant composition in a butanol fermentation process. The methods comprise (a) providing a fermentation medium comprising a fermentable carbon source, a recombinant microorganism comprising a butanol biosynthetic pathway, and butanol; (b) providing an extractant composition comprising an effective amount of antioxidant or antioxidant-like compound, wherein the antioxidant or antioxidant like compound increases the butanol partition coefficient of the extractant; and (c) contacting the fermentation medium of (a) with the extractant composition of (b) whereby increased levels of butanol partition into the extractant composition as compared to the levels of butanol partitioning in an extractant composition that does not comprise an effective amount of antioxidant or antioxidant-like compound or an extractant composition that does not comprise an antioxidant or antioxidant like compound that increases the butanol partition coefficient of the extractant.

Also provided are methods for reducing microbial contamination in a butanol fermentation process. The methods comprise (a) providing a fermentation medium comprising a fermentable carbon source, a recombinant microorganism comprising a butanol biosynthetic pathway, and butanol; (b) providing an extractant composition comprising an effective amount of antioxidant or antioxidant-like compound, wherein the antioxidant or antioxidant-like compound comprises antimicrobial activity; and (c) contacting the fermentation medium of (a) with the extractant composition of (b) whereby microbial contamination of a butanol fermentation is reduced as compared to a butanol fermentation utilizing an extractant composition that does not comprise an effective amount of antioxidant or antioxidant-like compound or an extractant composition that does not comprise an antioxidant or antioxidant-like compound with antimicrobial activity.

Further provided are biphasic compositions. The biphasic compositions can comprise (a) a first phase comprising a fermentation medium comprising a fermentable carbon source, a recombinant microorganism comprising an engineered biosynthetic pathway for producing a product alcohol, and a product alcohol; and (b) a second phase comprising an extractant composition comprising an effective amount of antioxidant or antioxidant-like compound, product alcohol, and free fatty acids, wherein the free fatty acids and antioxidant or antioxidant-like compound are derived from the fermentable carbon source. Optionally, the engineered biosynthetic pathway is a butanol biosynthetic pathway and the product alcohol is butanol.

FIGURE DESCRIPTION

Figure 4A:
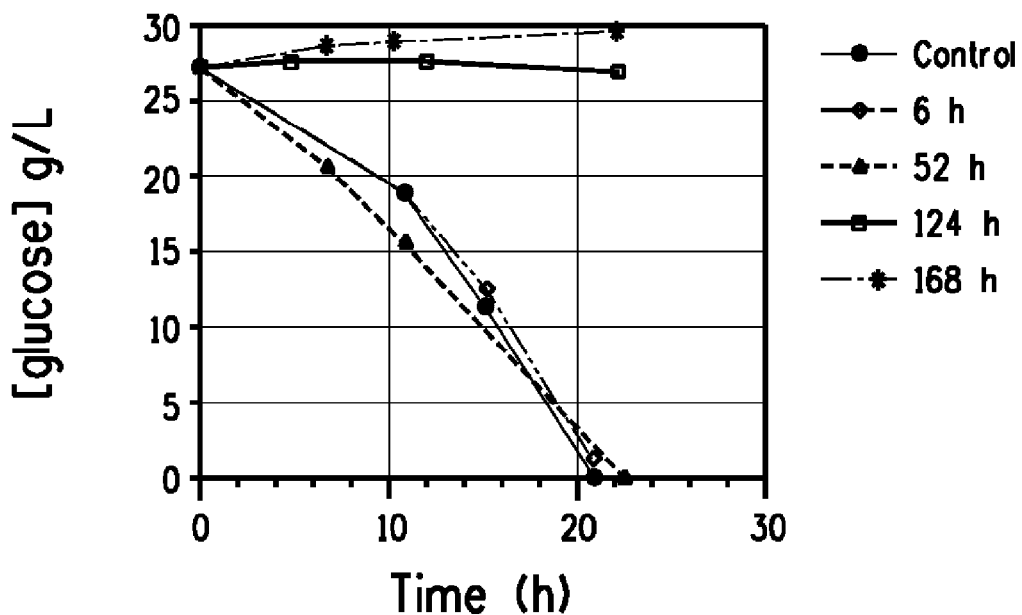
Figure 4B:
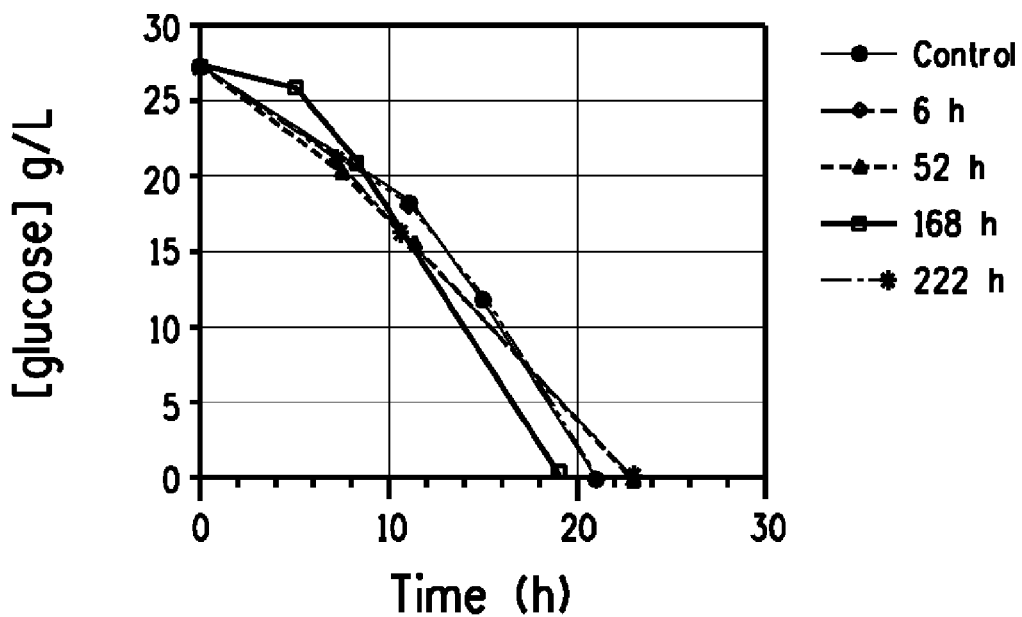
Figure 4C:
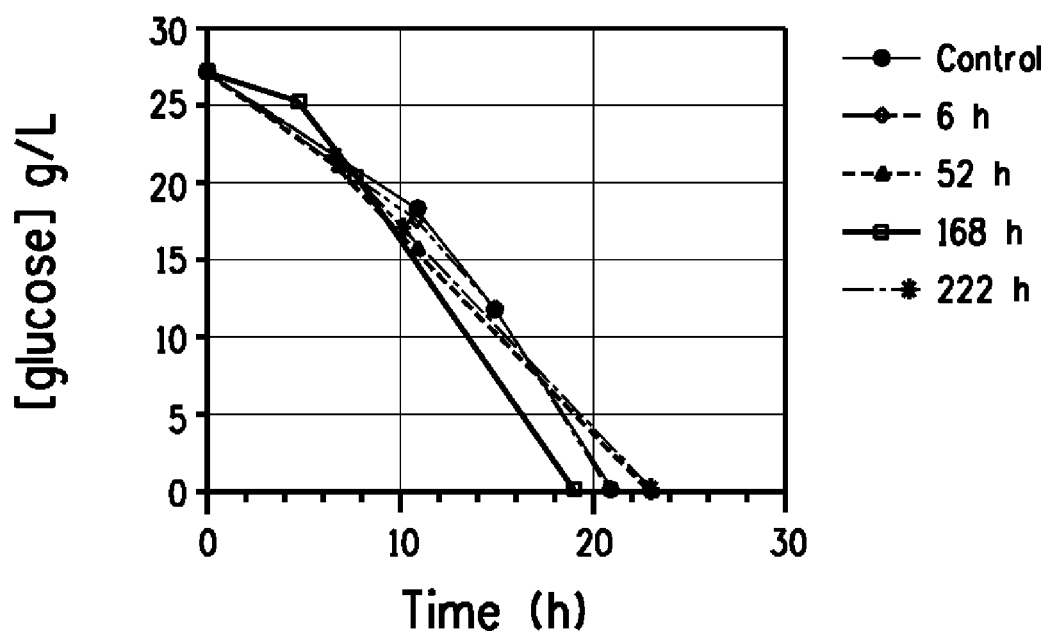

FIG. 4A shows a graph demonstrating carbon consumption for a butanologen grown in the presence of crude COFA sparged with air for the indicated times. FIG. 4B shows a graph demonstrating carbon consumption for a butanologen grown in the presence of COFA with 0.2 wt % BHT sparged with air for the indicated times. FIG. 4C shows a graph demonstrating carbon consumption for a butanologen grown in the presence of COFA with 0.8% wt % BHT sparged with air for the indicated times.

Figure 5:
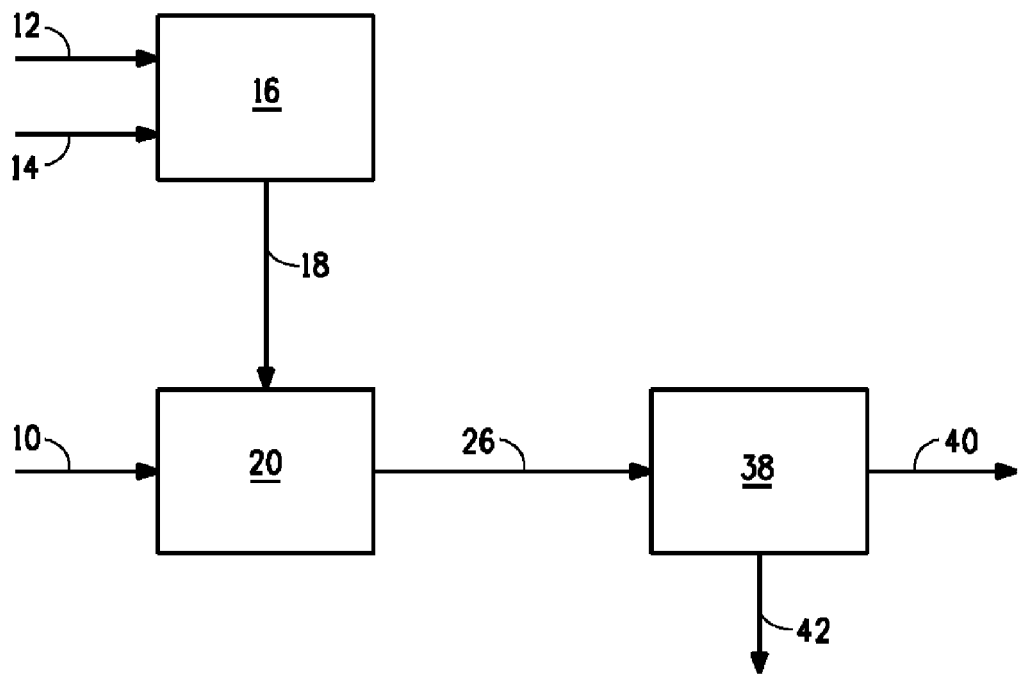

FIG. 5 schematically illustrates one embodiment of the methods of the invention, in which the first water immiscible extractant and the optional second water immiscible extractant are combined in a vessel prior to contacting the fermentation medium with the extractant in a fermentation vessel.

Figure 6:
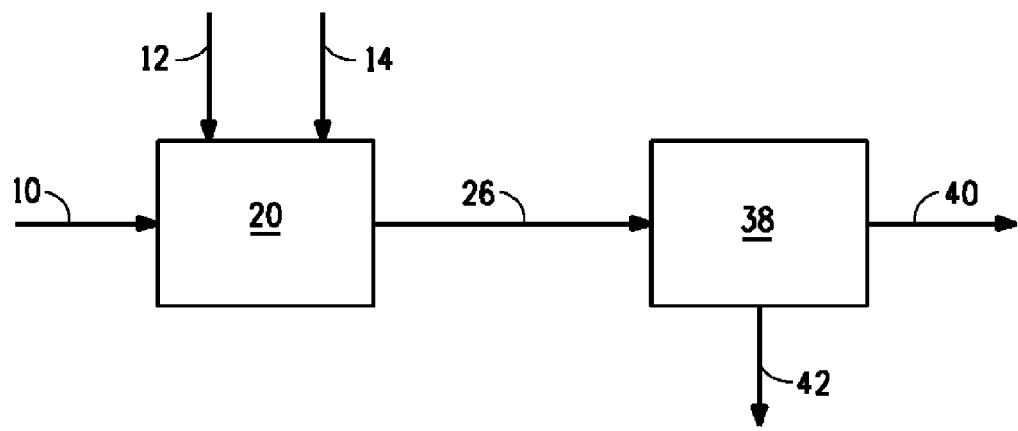

FIG. 6 schematically illustrates one embodiment of the methods of the invention, in which the first water immiscible extractant and the optional second water immiscible extractant are added separately to a fermentation vessel in which the fermentation medium is contacted with the extractant.

Figure 7:
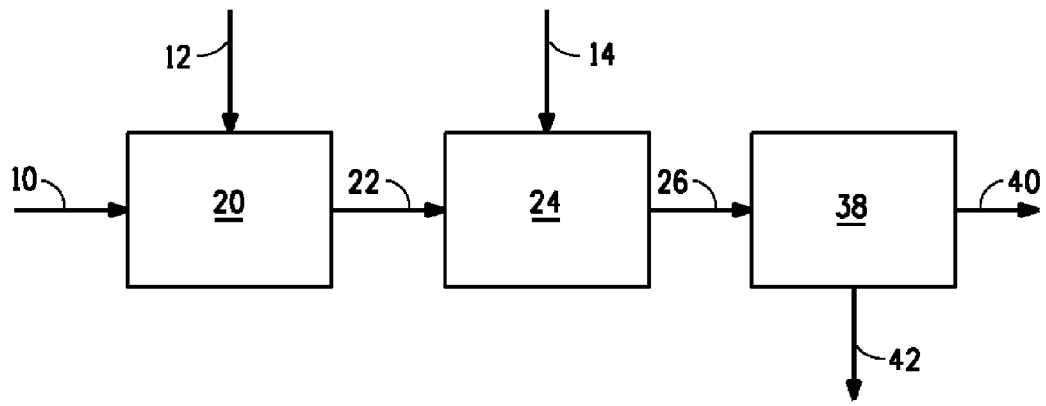

FIG. 7 schematically illustrates one embodiment of the methods of the invention, in which the first water immiscible extractant and the optional second water immiscible extractant are added separately to different fermentation vessels for contacting of the fermentation medium with the extractant.

Figure 8:
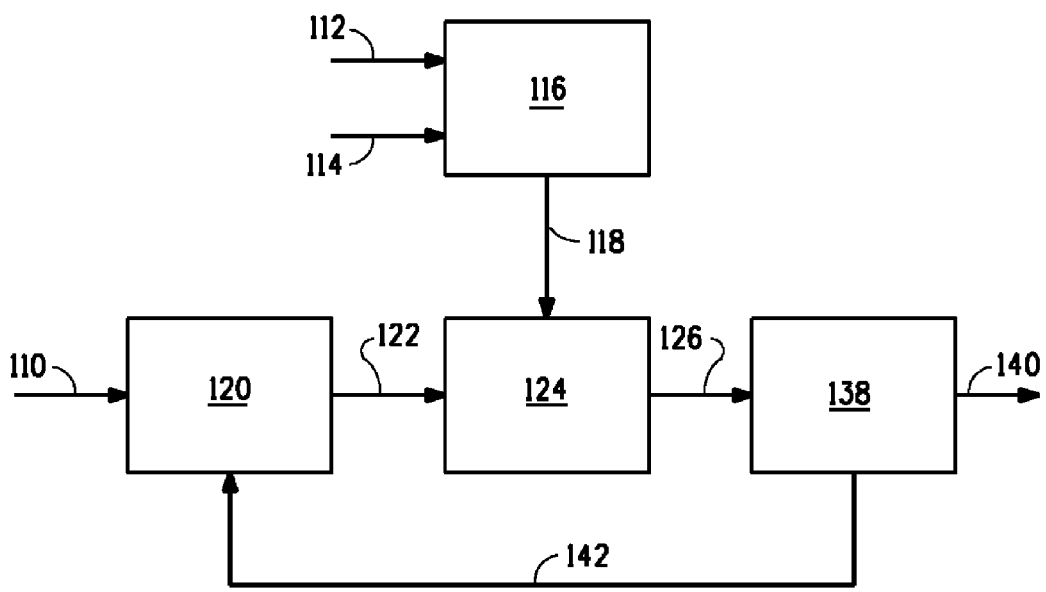

FIG. 8 schematically illustrates one embodiment of the methods of the invention, in which extraction of the product occurs downstream of the fermentor and the first water immiscible extractant and the optional second water immiscible extractant are combined in a vessel prior to contacting the fermentation medium with the extractant in a different vessel.

Figure 9:
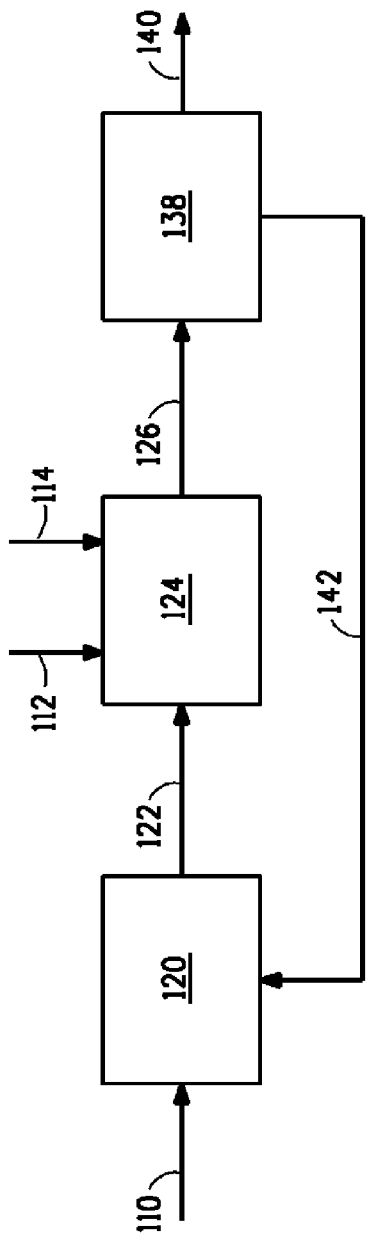

FIG. 9 schematically illustrates one embodiment of the methods of the invention, in which extraction of the product occurs downstream of the fermentor and the first water immiscible extractant and the optional second water immiscible extractant are added separately to a vessel in which the fermentation medium is contacted with the extractant.

Figure 10:
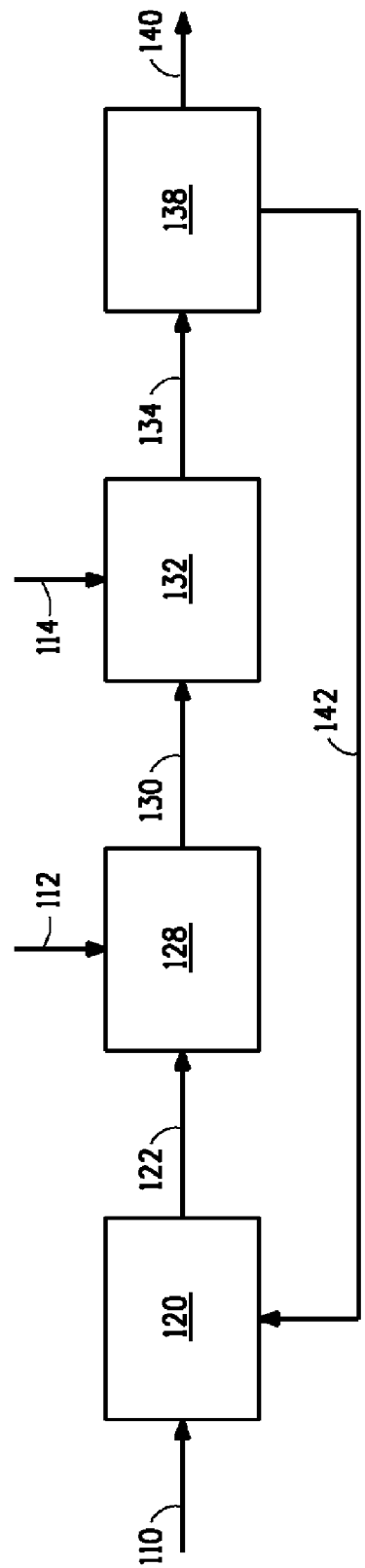

FIG. 10 schematically illustrates one embodiment of the methods of the invention, in which extraction of the product occurs downstream of the fermentor and the first water immiscible extractant and the optional second water immiscible extractant are added separately to different vessels for contacting of the fermentation medium with the extractant.

DETAILED DESCRIPTION

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein, is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture.

Whether or not modified by the term "about," the claims include equivalents to the quantities. In one embodiment, the term "about" means within 10% of the reported numerical value, alternatively within 5% of the reported numerical value.

The term "aerobic conditions" as used herein, means growth conditions in the presence of oxygen.

The term "microaerobic conditions" as used herein, means growth conditions with low levels of oxygen (i.e., below normal atmospheric oxygen levels).

The term "anaerobic conditions" as used herein, means growth conditions in the absence of oxygen.

"Biomass" as used herein, refers to a natural product comprising hydrolysable polysaccharides that provide fermentable sugars, including any sugars and starch derived from natural resources such as corn, sugar cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components, such as protein and/or lipids. Biomass may be derived from a single source, or biomass can comprise a mixture derived from more than one source; for example biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, waste sugars, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, whey, whey permeate, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation, such as by milling, treating and/or liquefying and comprises fermentable sugar and may comprise an amount of water. For example, corn may be processed via wet mill or dry mill and subsequently liquefied to produce mash. Cellulosic and/or lignocellulosic biomass may be processed to obtain a hydrolysate containing fermentable sugars by any method known to one skilled in the art (see, e.g., U.S. Patent Application Publication No. 2007/0031918, which is herein incorporated by reference). Enzymatic saccharification of cellulosic and/or lignocellulosic biomass makes use of an enzyme consortium for breaking down cellulose and hemicellulose to produce a hydrolysate containing sugars including glucose, xylose, and arabinose. Saccharification enzymes suitable for cellulosic and/or lignocellulosic biomass are reviewed in Lynd et al., Microbiol. Mol. Biol. Rev. 66:506-77 (2002).

The term "biomass" as used herein, in some instances, refers to the mass of the culture, e.g., the amount of recombinant microorganisms, typically provided in units of grams per liter (g/l) dry cell weight (dcw).

"Biomass yield" as used herein, refers to the ratio of microorganism biomass produced (i.e., cell biomass production) to carbon substrate consumed.

"Biofuel" or "biofuel product" as used herein, refers to a fuel derived from a biological process, for example, but not limited to, fermentation.

"Butanol" as used herein, refers to the butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or as mixtures thereof. From time to time, as used herein the term "biobutanol" may be used synonymously with "butanol."

"Product alcohol" as used herein, refers to any alcohol that can be produced by a microorganism in a fermentation process that utilizes biomass as a source of fermentable carbon substrate. Product alcohols include, but are not limited to, $C_1$ to $C_8$ alkyl alcohols, and mixtures thereof. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, pentanol, and mixtures thereof. Likewise $C_2$ to $C_8$ alkyl alcohols include, but are not limited to, ethanol, propanol, butanol, and pentanol. "Alcohol" is also used herein with reference to a product alcohol.

The term "effective titer" as used herein, refers to the total amount of a particular alcohol (e.g., butanol) produced by fermentation or alcohol equivalent of the alcohol ester produced by alcohol esterification per liter of fermentation medium. For example, the effective titer of butanol in a unit of volume of a fermentation includes: (i) the amount of butanol in the fermentation medium; (ii) the amount of butanol recovered from the organic extractant; (iii) the amount of butanol recovered from the gas phase, if gas stripping is used; and (iv) the alcohol equivalent of the butyl ester in either the organic or aqueous phase.

The term "effective rate" as used herein, is the effective titer divided by the fermentation time.

The term "effective yield" as used herein, is the total grams of product alcohol produced per gram of glucose consumed.

The term "butanol biosynthetic pathway" as used herein refers to the enzymatic pathway to produce 1-butanol, 2-butanol, or isobutanol.

The term "1-butanol biosynthetic pathway" refers to an enzymatic pathway to produce 1-butanol. A "1-butanol biosynthetic pathway" can refer to an enzyme pathway to produce 1-butanol from acetyl-coenzyme A (acetyl-CoA). For example, 1-butanol biosynthetic pathways are disclosed in U.S. Patent Application Publication No. 2008/0182308 and International Publication No. WO 2007/041269, which are herein incorporated by reference in their entireties.

The term "2-butanol biosynthetic pathway" refers to an enzymatic pathway to produce 2-butanol. A "2-butanol biosynthetic pathway" can refer to an enzyme pathway to produce 2-butanol from pyruvate. For example, 2-butanol biosynthetic pathways are disclosed in U.S. Pat. No. 8,206,970, U.S. Patent Application Publication No. 2007/0292927, International Publication Nos. WO 2007/130518 and WO 2007/130521, which are herein incorporated by reference in their entireties.

The term "isobutanol biosynthetic pathway" refers to an enzymatic pathway to produce isobutanol. An "isobutanol biosynthetic pathway" can refer to an enzyme pathway to produce isobutanol from pyruvate. For example, isobutanol biosynthetic pathways are disclosed in U.S. Pat. No. 7,851,188, U.S. Pat. No. 7,993,889, U.S. Application Publication No. 2007/0092957, and International Publication No. WO 2007/050671, which are herein incorporated by reference in their entireties. From time to time "isobutanol biosynthetic pathway" is used synonymously with "isobutanol production pathway."

"In Situ Product Removal" (ISPR) as used herein, means the selective removal of a fermentation product from a biological process such as fermentation to control the product concentration as the product is produced.

"Fermentable carbon source" or "fermentable carbon substrate" as used herein, means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; amino acids; and mixtures thereof.

"Feedstock" as used herein, means a feed in a fermentation process, the feed containing a fermentable carbon source with or without undissolved solids, and where applicable, the feed containing the fermentable carbon source before or after the fermentable carbon source has been liberated from starch or obtained from the breakdown of complex sugars by further processing such as by liquefaction, saccharification, or other process. Feedstock includes or is derived from a biomass. Suitable feedstocks include, but are not limited to, rye, wheat, corn, corn mash, cane, cane mash, barley, cellulosic material, lignocellulosic material, or mixtures thereof. Where reference is made to "feedstock oil," it will be appreciated that the term encompasses the oil produced from a given feedstock.

"Sugar" as used herein, refers to oligosaccharides, disaccharides, monosaccharides, and/or mixtures thereof. The term "saccharide" also includes carbohydrates including starches, dextrans, glycogens, cellulose, pentosans, as well as sugars.

"Fermentable sugar" as used herein, refers to one or more sugars capable of being metabolized by the microorganisms disclosed herein for the production of fermentative alcohol.

"Undissolved solids" as used herein, means non-fermentable portions of feedstock, for example, germ, fiber, and gluten. For example, the non-fermentable portions of feedstock include the portion of feedstock that remains as solids and can absorb liquid from the fermentation broth.

"Fermentation medium" as used herein, means the mixture of water, sugars, dissolved solids, optionally microorganisms producing alcohol, product alcohol, and all other constituents of the material in which product alcohol is being made by the reaction of sugars to alcohol, water, and carbon dioxide ($CO_2$) by the microorganisms present. From time to time, as used herein the term "fermentation broth" and "fermented mixture" can be used synonymously with "fermentation medium." Fermentation medium may also include antioxidant capable of preventing or reducing the oxidation rate of unsaturated fatty acids in the extractant composition.

The term "biphasic fermentation medium" as used herein, refers to a two-phase growth medium comprising a fermentation medium (i.e., aqueous phase) and a suitable amount of a water immiscible organic extractant.

"Fermentation vessel" as used herein, means the vessel in which a fermentation reaction is carried out whereby product alcohol such as butanol is made from sugars. "Fermentor" may be used herein interchangeable with "fermentation vessel."

The term "recovery," "recovering," or variants thereof refers to removing a chemical compound from an initial mixture to obtain the compound in greater purity or at a higher concentration than the purity or concentration of the compound in the initial mixture.

"Extractant" as used herein, means a solvent used to remove or separate a product alcohol such as butanol. From time to time, as used herein the term "solvent" may be used synonymously with "extractant." For the processes described herein, extractants are water immiscible.

"Water immiscible" or "insoluble" as used herein, refers to a chemical component such as an extractant or solvent, which is incapable of mixing with an aqueous solution such as a fermentation broth, in such a manner as to form one liquid phase.

The term "aqueous phase" as used herein, refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction, and the terms "solvent-poor phase" may be used synonymously with "aqueous phase" and "fermentation broth." In addition, undissolved solids (e.g., grain solids) can be present in the fermentation broth, such that the biphasic mixture includes the undissolved solids which are primarily dispersed in the aqueous phase.

The term "organic phase" as used herein, refers to the non-aqueous phase of a biphasic mixture obtained by contacting a fermentation broth with a water-immiscible organic extractant. From time to time, as used herein the terms "solvent-rich phase" may be used synonymously with "organic phase."

The term "fatty acid" as used herein, refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein, refers to an alcohol having an aliphatic chain of $C_4$ to $C_{22}$ carbon atoms, which is either saturated or unsaturated.

The term "fatty aldehyde" as used herein, refers to an aldehyde having an aliphatic chain of $C_4$ to $C_{22}$ carbon atoms, which is either saturated or unsaturated.

The term "fatty amide" as used herein, refers to an amide having a long, aliphatic chain of $C_4$ to $C_{22}$ carbon atoms, which is either saturated or unsaturated.

The term "fatty ester" as used herein, refers to an ester having a long aliphatic chain of $C_4$ to $C_{22}$ carbon atoms, which is either saturated or unsaturated.

The term "carboxylic acid" as used herein, refers to any organic compound with the general chemical formula —COOH in which a carbon atom is bonded to an oxygen atom by a double bond to make a carbonyl group (—C═O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

"Portion" as used herein, includes a part of a whole or the whole. For example, a portion of fermentation broth includes a part of the fermentation broth as well as the whole (or all) the fermentation broth.

"Partition coefficient" refers to the ratio of the concentration of a compound in the two phases of a mixture of two immiscible solvents at equilibrium. A partition coefficient is a measure of the differential solubility of a compound between two immiscible solvents. Partition coefficient, as used herein, is synonymous with the term distribution coefficient.

As used herein, the term "antimicrobial activity" refers to an ability of a compound and/or molecule to kill a microorganism or inhibit microbial growth. Methods for determining antimicrobial activity are known in the art, e.g., disc diffusion assays, agar dilution assays, broth dilution assays, and inhibition zone assays.

As used herein, the term "recombinant microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

An "effective amount of antioxidant or antioxidant-like compound" as used herein, refers to a level of antioxidant (e.g., a compound, substance, or molecule) or antioxidant-like compound (e.g., amino acids) capable of quenching the peroxy radical formed during the oxidation of unsaturated fatty acids or the secondary reactive products of the peroxy radical (e.g., aldehydes and ketones). By quench, it is meant that the antioxidant or antioxidant-like compound prevents, reduces, or neutralizes the activity of a peroxy radical or a secondary reactive product of the peroxy radical.

An "antioxidant-like compound" as used herein, refers to a compound that is capable of reacting and neutralizing the secondary oxidation products of an oxidation reaction (e.g., aldehydes or ketones). By way of an example, the amino group of amino acids can react with aldehydes or ketones to quench or counteract the effect of the aldehydes or ketones.

"Oxidized products" as used herein, refers to hydroperoxides, peroxides, aldehydes, ketones, and/or polymerization products formed from the peroxides.

In the present case, an effective amount of antioxidant or antioxidant-like compound in an extractant can be determined by measuring the growth rate or effective yield of a recombinant microorganism in a fermentation process with a recycled extractant. A baseline level of growth or effective yield of a recombinant microorganism can be determined in a fermentation process prior to the exposure of a recycled extractant. This baseline level of growth or effective yield can be used to determine whether the recycled extractant comprises a deficiency in the level of antioxidants or antioxidant-like compounds. By way of an example, a reduction in the growth or effective yield of the recombinant microorganism in a fermentation process, wherein the recombinant microorganism is exposed to a recycled extractant, as compared to the growth or effective yield of the recombinant microorganism prior to the exposure to the recycled extractant indicates a deficiency in the level of antioxidants or antioxidant-like compounds in the extractant. The reduction in growth and/or effective yield of the recombinant microorganism can be compared to the growth and/or effective yield of the previous fermentation with the same recombinant microorganism and extractant prior to the recycling of the extractant. Alternatively, the reduction in growth or effective yield of the recombinant microorganism can be compared to the standard growth or effective yield of the same recombinant microorganism in a standard extractant with an effective amount of antioxidants or antioxidant-like compounds. By way of another example, in a fermentation process, wherein the extractant is recycled multiple times, the growth and effective yield of the microorganism can be monitored to determine if the extractant maintains an effective level of antioxidants or antioxidant-like compounds after each recycle by comparing the growth and effective yield of the recombinant microorganism to the previous growth and effective yield. A reduction in the growth or effective yield indicates that the extractant comprises a deficiency in the level of antioxidants or antioxidant-like compounds.

In certain embodiments, an effective amount of antioxidant or antioxidant-like compound can be indicated by measuring the rate of loss of oxidation sensitive components of the extractant (e.g., the loss of the linoleic 18:2 in corn oil fatty acid (COFA)) relative to the loss of those components in a sample of extractant that does not contain an antioxidant or antioxidant-like compound. An extractant composition with an effective amount of antioxidant or antioxidant-like compound is indicated where the rate of loss of oxidation sensitive components relative to the rate of loss of oxidation sensitive components in an extractant without antioxidants or antioxidant-like compounds is less than about 0.9, preferably the ratio is less than about 0.5, more preferably the ratio is less than about 0.2, and most preferably the ratio is less than about 0.1. The rate can be determined by determining the amount of each component of the extractant (e.g., the amount of linoleic 18:2) before and after each recycle. Analytical GC using AOCS method Ce 1e-91 combined with AOCS method Ce2-66 or similar methods can be used to determine the amounts of each component with fatty acid and fatty ester based extractants, but other techniques would be apparent to one skilled in the art.

In certain embodiments, an effective amount of antioxidant or antioxidant-like compound can be determined by measuring the peroxide content, the aldehyde content, and/or ketone content of the extractant at each recycle of the extractant. An increase in the peroxide content, aldehyde content, and/or ketone content of the extractant over time as compared to a control indicates a deficiency in the level of antioxidants or antioxidant-like compounds of the extractant. A control, as used herein, can include the measurement of the peroxide content, aldehyde content, and/or ketone content of the extractant prior to the recycling of the extractant or the peroxide, aldehyde, and/or ketone content of the extractant in the previous recycle. Alternatively, a control can include the baseline peroxide content, aldehyde content, and/or ketone content of an extractant prior to use of the extractant, wherein the extractant comprises an effective amount of antioxidants or antioxidant-like compounds.

In certain embodiments, an effective amount of the antioxidant or antioxidant-like compound can be determined by measuring the level of the antioxidant or antioxidant-like compound. A decrease in the level of the antioxidant or antioxidant-like compound over time (i.e., each recycle of the extractant) can be measured and monitored based on the initial effective level of antioxidant or antioxidant-like compound in the extractant prior to use of the extractant. A person skilled in the art can determine an effective level of antioxidant or antioxidant-like compound experimentally and monitor the extractant to ensure that the level of antioxidant or antioxidant-like compound does not go below the effective level determined. Methods to determine the level of antioxidant or antioxidant-like compound are known in the art and can include, but are not limited to, gas chromatography (GC), high pressure liquid chromatography (HPLC), ultra violet spectroscopy (UV), or infra-red spectroscopy (IR).

"Antioxidative activity index" refers to a measure of the effectiveness of an antioxidant or antioxidant mixture at slowing the rate of oxidation of an oxidizable oil. The antioxidative activity index can, for example, be determined using the Rancimat method. The Rancimat method determines the ratio of the induction time prior to oxidation of the oil with 200 ppm of the antioxidant divided by the induction time of the unfortified oil. The Rancimat method is known in the art, for example, see "Determination of antioxidant activity by the Rancimat method," Application Bulletin, Metrohm, No. 232/1, pages 1-3.

In a fermentation process where liquid-liquid extraction is performed, it may be desirable to recycle the extractant. As described in United States Patent Application Nos. 2009/0305370A1 and 2011/0312043A1, $C_{12}$ to $C_{22}$ fatty acids are exemplified to be useful as an extractant, and, processes which utilize feedstocks (e.g., corn) advantageously capitalize on materials present in the feedstock which would otherwise be excess materials. Processes described herein allow repeated recycle of such extractants, further improving the efficiency and advantages of processes employing liquid-liquid extraction with extractants that, for example, comprise $C_{12}$ to $C_{22}$ fatty acids.

For example, in a fermentation process, the extractant for recovering butanol from the fermentation may be oxidized. While not intending to be bound by theory, oxidation can, for example, be due to exposure to aerobic fermentation conditions and/or the presence of oxygen during any process step in the production. Oxidation of the extractant composition can result in the production of unwanted peroxides, aldehydes, ketones, and radicals in the extractant composition, which can be harmful to the microorganism responsible for fermentation. The rate of oxidation of the extractant composition can be counteracted or slowed by antioxidants or antioxidant-like compounds within the extractant composition; however, recycling of the extractant can result in the depletion or loss of antioxidants or antioxidant-like compounds in the extractant composition.

To reduce the rate of oxidation of the recycled extractant, the extractant can be exposed to a reduced level of oxygen or the extractant is utilized in an environment free of oxygen. To reduce the level of exposure of the extractant to oxygen, the liquids in the fermentation process (e.g., fermentation broth, extractant, water) can be degassed or purged with a gas that does not contain oxygen. Additionally, aeration of the fermentation vessels can be reduced or eliminated.

To reduce the rate of oxidation of an extractant, the extractant can be stored in storage tanks blanketed with an inert atmosphere devoid of oxygen. For example, an extractant storage tank can comprise an inert atmosphere consisting mainly or entirely of nitrogen, carbon dioxide, an inert gas (e.g., helium, neon, argon, krypton, xenon), or combinations thereof. Carbon dioxide could be derived from the fermentation process as an off gas produced by the recombinant microorganism. A person skilled in the art can determine an inert atmosphere for the storage tank that is conducive for reducing or eliminating oxidation of the extractant.

The present invention is related to processes for maintaining or providing an effective amount of antioxidant or antioxidant-like compound in an extractant to recover butanol from a fermentation process. The processes comprise (a) providing a fermentation medium comprising a fermentable carbon source, a recombinant microorganism comprising an engineered butanol biosynthetic pathway, and butanol; (b) contacting said fermentation medium with an extractant composition comprising an effective amount of antioxidant or antioxidant-like compound, whereby at least a portion of the butanol in the fermentation medium partitions into the extractant; (c) recovering at least a portion of the butanol and extractant composition from the fermentation medium; (d) recycling the extractant composition recovered in (c) one or more times to the fermentation medium; and (e) optionally adjusting the effective amount of the antioxidant or antioxidant-like compound in the extractant composition, whereby the rate of formation of oxidized products or the effect of the oxidized products in the recycled extractant composition is substantially reduced or avoided such that the extractant composition may be recycled as provided in step (d) for at least ten recycles.

Optionally, the extractant composition can be recycled for at least 20 recycles. Optionally, the extractant composition may be recycled for at least 50 recycles. Optionally, the extractant composition can be recycled for about 5 to about 100 recycles. Optionally, the extractant composition can be recycled for about 10 to about 80 recycles, for about 20 to about 60 recycles, or for about 30 to about 50 recycles.

In certain embodiments, the steps of the process can occur contemporaneously. By way of an example, steps (b) and (c) occur contemporaneously. By way of another example, steps (c) and (d) occur contemporaneously. By way of another example, steps (b), (c), and (d) occur contemporaneously.

In certain embodiments, the steps of the process can occur in the same vessel. By way of an example, steps (b) and (c) occur in the same vessel. By way of another example, steps (c) and (d) occur in the same vessel. By way of another example, steps (d) and (e) occur in the same vessel. By way of another example, steps (b), (c), (d), and (e) occur in the same vessel. The vessel can, for example, be a fermentation vessel.

In some embodiments, step (d) may occur downstream of step (c), while still occurring concurrently.

By adjusting the amount of antioxidant or antioxidant-like compound of the extractant, it is generally meant that the amount of antioxidant or antioxidant-like compound is increased. Adjusting the amount of antioxidant or antioxidant-like compound of the extractant composition can, for example, comprise supplementing the extractant composition with one or more antioxidants or antioxidant-like compounds. Supplementation may occur through addition of antioxidant or antioxidant-like compound to the extractant composition prior to addition to the fermentation vessel, during fermentation, or with extractant recycle. Supplementation may also occur by providing antioxidant or antioxidant-like compound with the biomass (e.g., corn mash), with fermentation medium, or produced by the recombinant microorganism engineered to produce butanol. In an embodiment, the feedstock (i.e., biomass) which is used as the carbon source for fermentation of butanol may be selected based on having an improved fatty acid profile and/or natural antioxidant or antioxidant-like composition, or may be genetically modified to provide a fatty acid profile that is less susceptible to oxidation or that includes an effective amount of antioxidant or antioxidant-like compound for improved extraction of butanol during fermentation.

Recycling the extractant composition is facilitated by preventing or reducing oxidation of the extractant that may be exposed to oxygen during recovery and/or other processing in butanol production. The extractant composition can be adjusted at each recycle of the extractant composition to maintain the oxidative state of the extractant composition (i.e., to prevent further oxidation or reduce the effect of oxidized products on the extractant). Alternatively, the extractant composition can be adjusted once such that it comprises an effective amount of antioxidant or antioxidant-like compound for at least 5 recycles, preferably 10 recycles, more preferably 20 recycles, most preferably 100 recycles. Alternatively, the extractant composition can be adjusted every other recycle. A person skilled in the art will be capable of determining at which recycle number a given extractant composition will need to be adjusted, which may include monitoring the oxidation state of the extractant composition. Determining the oxidation state of the extractant composition may be accomplished by monitoring the loss of one or more components of the extractant (e.g., the loss of linoleic 18:2 in corn oil fatty acid (COFA)) at each recycle. Optionally, determining the oxidation state of the extractant composition may be accomplished by monitoring the antioxidative activity index of the extractant at each recycle (e.g., by use of the Rancimat method). Optionally, determining the oxidation state of the extractant composition may be accomplished by monitoring one or more indicators of fermentation productivity, such as effective rate, effective titer, effective yield of product alcohol, in addition to measuring the growth rate (e.g., carbon consumption rate) or effective yield of a recombinant microorganism in the fermentation process or by chemical analysis for the presence of primary or secondary oxidation products of the oxidized extractant.

Supplementing the extractant composition with one or more antioxidants or antioxidant-like compounds can comprise addition of a fresh or unused portion of the same or a different extractant composition comprising an effective amount of antioxidant or antioxidant-like compounds to the extractant composition. Optionally, supplementing the extractant with one or more antioxidants or antioxidant-like compounds can comprise the addition of the one or more antioxidants or antioxidant-like compounds directly to the extractant composition. Amounts of the one or more antioxidants or antioxidant-like compounds or extractant composition comprising an effective amount of antioxidant or antioxidant-like compounds to be added to the extractant composition comprising an ineffective amount of antioxidant or antioxidant-like compound can be determined by those skilled in the art.

A key factor in the process of oxidation is oxygen. In the ground state, oxygen exists as a bi-radical and reacts readily with carbon free radicals to yield peroxy radicals. Unless these radical species are inhibited, organic substances, which have a strong tendency to react with oxygen and oxidize, can quickly deteriorate. Antioxidant compounds can inhibit the radical species that are responsible for the oxidation of organic substances. Antioxidants can be classified by the mechanism of action: primary or chain breaking antioxidants and secondary or preventative antioxidants. Some antioxidants can exhibit more than one mechanism of action. Antioxidants are known in the art, e.g., see Antioxidants, Peter P. Klemchuk, "Ullmann's Encyclopedia of Industrial Chemistry," Vol. 4; Wiley-VCH Verlag GmbH & Co., pp. 158-178 (2012); and Antioxidants: Science, Technology, and Applications, P. K. J. P. D. Wanasundara and F. D. Shahidi, "Bailey's industrial oil and fat products," $6^{th}$ Edi., Vol. 1, Chapter 11; John Wiley & Sons, Inc., pp. 431-489 (2005).

Primary antioxidants can be referred to as type 1 or chain-breaking antioxidants. Because of the chemical nature of the primary antioxidants, the compounds can act as free radical acceptors/scavengers and delay or inhibit the initiation step or interrupt the propagation step of autoxidation. Primary antioxidants cannot inhibit photosensitized oxidation or scavenge singlet oxygen. Primary antioxidants can have higher affinities for peroxy radicals than lipids and react predominantly with peroxy radicals at least for the following reasons. Propagation is the slow step in lipid oxidation process; thus, peroxy radicals can be found in comparatively larger quantities than other radicals. Additionally, peroxy radicals can have lower energies than alkoxy radicals; therefore, the peroxy radicals can react more readily with the low energy hydrogen of primary antioxidants than unsaturated fatty acids. As the free radical scavengers can be found in low concentration, the free radical scavengers may not compete effectively with initiating radicals (e.g., hydroxyl radicals). Therefore, primary antioxidants can inhibit lipid oxidation more effectively by competing with other compounds for peroxy radicals, and the primary antioxidants can be capable of scavenging peroxy- and alkoxy-free radicals formed during propagation and other reactions in autoxidation.

The compounds that exhibit primary antioxidant activity can include polyhydroxy phenolics, unhindered, or hindered phenolics. There are several synthetic ring substituted phenolics as well as naturally occurring phenolic compounds that may perform via the primary antioxidant mechanism. The common feature of the primary antioxidants is that they are mono or polyhydroxy phenols with various ring substitutes. Substitution with electron-donating groups ortho and/or para to the hydroxyl group of phenol can increase the antioxidant activity of the compound by an inductive effect (e.g., 2,6-di-tert-butyl-4-methylphenol or BHA). The presence of a second hydroxyl group in the 2-(ortho) or the 4-position (para) of a phenol can increase the antioxidant activity (e.g., TBHQ). Carotenoids, flavonoids, phenolic acids, tocopherols and tocotrienols are natural primary antioxidants used in foods. Synthetic primary antioxidants that can be used in foods also include, but are not limited to butylated hydroxyanisole (BHA), butylated hydroxytoluene (BHT), ethoxyquin, propyl gallate (PG), and tertiary-butylhydroquinone (TBHQ). Substitution with butyl or ethyl groups para to the hydroxyl groups can also enhance the antioxidant activity. Substitution of branched alkyl groups at ortho positions can enhance the ability of the molecule to form a stable resonance structure that can reduce the participation of the radical in propagation reactions.

Secondary antioxidants can be referred to as preventive or class II antioxidants. Secondary antioxidants can work through various mechanisms to slow the rate of oxidation reactions. The main difference with primary antioxidants is that the secondary antioxidants do not convert free radicals into stable molecules. Secondary antioxidants can act as chelators for pro-oxidant or catalyst metal ions, provide hydrogen to primary antioxidants, decompose hydroperoxide to nonradical species, deactivate singlet oxygen, absorb ultraviolet radiation, or act as oxygen scavengers. Secondary antioxidants can enhance the antioxidant activity of primary antioxidants. Examples of secondary antioxidants can include, but are not limited to cirtic, malic, succinic and tartaric acids; ethylenediaminetetraacetic acid; phosphates; ascorbic acid, ascorbyl palmitate; erythorbic acid; sodium erythorbate; sulfites; and carotenoids (e.g., (3-carotene, lycopene, and lutein).

Examples of antioxidants can be selected from, but are not limited to, the group consisting of tocopherols, tocotrienols, amino acids with antioxidant activity, butylated hydroxyanisole (BHA), butylated hydroxytoluene (BHT), other alkylated phenols, epigallocatechin gallate (EGCG), epigallocatechin (EGC), epicatechin gallate (ECG), gallic acid, gallic esters (e.g., propyl gallate), carnosol, carnosic acid, ursolic acid, tanshen I, dihydrotanshinone, tanshinone HA, tanshinone IIB, danshenxinkun B, peroxidase enzymes, immobilized borohydrides, L-ascorbic acid 6-palmitate, anthocyanidins, anthocyanins, ethoxyquin, tertiary-butylhydroquinone (TBHQ) and combinations thereof. In certain embodiments, the one or more antioxidants can be tocopherols. In certain embodiments, the one or more antioxidants can comprise BHT. In certain embodiments, the one or more antioxidants can comprise a combination of BHT and BHA.

Antioxidants can be selected for based on other advantageous properties of the antioxidant or antioxidant-like compound. Other advantageous properties can include, but are not limited to, the ability to increase the butanol partition coefficient for the extractant (i.e., can act as a co-extractant), antimicrobial activity of the antioxidant or antioxidant-like compound, the ability to increase/improve phase separation during two-phase extraction of product alcohol, and an increased affinity for the extractant during product alcohol purification process (i.e., the antioxidant or antioxidant-like compound remains in the extractant during purification of the product alcohol). Certain classes of antioxidants can enhance the extraction efficiency for butanol. Addition of antioxidant or antioxidant-like compounds that increase the butanol partition coefficient can lead to improved extraction of the butanol. Examples of types of antioxidants which can provide beneficial effects in increasing the butanol partition coefficient for the extractant can include phenolic type antioxidants. The phenolic type antioxidants can include unhindered and partially hindered phenols. Unhindered and partially hindered phenols are known in the art, see, e.g., U.S. Pat. No. 3,536,662, U.S. Pat. No. 4,744,881.

Certain classes of antioxidants can provide both antioxidant and antimicrobial benefits for the extractant. Addition of the antioxidant or antioxidant-like compounds that have antimicrobial activity can lead to improvements in the production of butanol. By way of an example, antioxidants, such as butylated hydroxytoluene (BHT) have antimicrobial activity towards gram-negative and gram-positive bacteria (e.g., *Lactobacillus*), but does not affect yeast (e.g., *Saccharomyces*). Antimicrobial activity for antioxidants has been shown in the art, e.g., see, Fung et al, CRC Critical Reviews Microbiol. 12(2):153-83 (1985); Sankaran, J. Food Science Technol. 13:203-4 (1976); Yankah et al., Lipids AOC Press 33(11): 1139-1145 (1998).

Optionally, the one or more antioxidants or antioxidant-like compounds can be amino acids. Amino acids with antioxidant activity can include, but are not limited to, cysteine, methionine, phenylalanine, histidine, tryptophan, and tyrosine. Free amino acids with antioxidant or antioxidant-like activity can be added with the extractant composition. Optionally, in the fermentation process, the fermentable carbon source is provided by processing the biomass, and the biomass can be further processed by the addition of enzymes or other agents which produce antioxidant or antioxidant-like compounds from the biomass. Optionally, a protease is added to the biomass, whereby addition of the protease stimulates the release of free amino acids from the biomass, which provides antioxidant or antioxidant-like activity for the extractant composition. Without intending to be limited by theory, free amino acids can act as antioxidant like compounds by reacting with the lipid peroxidation-derived aldehydes neutralizing the impact of the aldehydes on the recombinant microorganism, and the free amino acids with antioxidant activity can quench reactive oxygen radicals via oxidation of the free side chains of the free amino acids (e.g., cysteine, methionine, and the aromatic amino acids). Further, addition of proteases to the biomass can make additional free amino nitrogen in the form of amino acids available to the recombinant microorganism, which can increase cell growth rates and butanol production, as it has been shown to increase ethanol production in ethanologens (see, e.g., Piddocke et al., Microb. Cell Fact. 10:27 (2011)).

The protease can, for example, be deactivated at a temperature of at least 85° C. Deactivation of the protease can take at least 15 minutes at a temperature of at least about 85° C. Methods to deactivate proteases are known in the art. The protease can, for example, be deactivated prior to the introduction of the recombinant microorganism for the fermentation process. Without intending to be limited by theory, deactivation of the protease prior to the introduction of the recombinant microorganism can prevent unwanted cell death of the recombinant microorganism.

Optionally, the protease is a universal protease capable of hydrolyzing all amino acid bonds in a polypeptide. Examples of universal proteases can include, but are not limited to, Pronase®, Fermgen®, and Flavourzyme®. Universal proteases are known in the art.

An alcohol production process wherein substrates containing proteins, for example, feedstock solids, can be modified to include a step wherein the biomass feedstock is subjected to chemical or enzymatic hydrolysis to yield protein hydrolysates for use in the present processes. For example, protein hydrolysates may be generated from substrates present in the fermentation vessel, in the thin stillage, in the whole stillage wet cake, in the syrup, in the backset, or in the wet cake.

Protein hydrolysates (i.e., mixtures of peptides and amino acids) are typically produced from polypeptides during processes of chemical hydrolysis or enzymatic hydrolysis, as described further below. According to the processes of the present invention, protein hydrolysates can be produced via hydrolysis of various process streams (e.g., feedstock slurry, wet cake, within the fermentor, whole stillage wet cake, thin stillage, and/or syrup).

Chemical Hydrolysis:

Polypeptides can be completely hydrolyzed by chemical methods, for example, those that are used for amino acid analysis. These include liquid phase and vapor phase acid hydrolysis using 6 N HCl at 110° C. or at higher temperature for shorter times. Polypeptide hydrolysis may also be accelerated by use of microwave heating. Hydrolyses are typically performed as a function of time as serine and threonine are labile and peptide bonds where P1 is isoleucine or valine and P1' is isoleucine or valine cleave slowly. Following a time course allows one to determine the rate of degradation of serine and threonine and the rate of cleavage of isoleucine and valine. Asparagine and glutamine are hydrolyzed to the respective aspartic and glutamic acids. Cysteine is oxidized to cystine and some oxidation of methionine will occur to the sulfone. Tryptophan is particularly labile to oxidation but can be stabilized to some extent in the presence of thiol reagents (e.g., mercaptoethanesulfonic acid, thioglycolic acid).

Enzymatic Hydrolysis:

Complete enzymatic conversion of a polypeptide to its component amino acids is often more difficult than acid hydrolysis, owing to the specificity of different proteases. Treatment by broad spectrum proteases (e.g., proteinase K, papain, subtilisin) or consortia of endopeptidases (e.g., pepsin, trypsin, chymotrypsin, and elastase), followed by a combination of exopeptidases (e.g., carboxypeptidases and aminopeptidases) and dipeptidyl and tripeptidyl peptidases are likely to yield a fairly complete hydrolysis, though there may be at the same time some autoproteolysis or cross proteolysis of the added proteases. Pronase, a mixture of proteases secreted by *Streptomyces griseus* will give a complete or nearly complete hydrolysis of many polypeptides. The choice and concentration of the proteases used may need to be tailored to the polypeptide to be hydrolyzed.

Described in U.S. Pat. No. 5,231,017 is a process for producing ethanol from raw materials that contain fermentable sugars or constituents which can be converted to sugars, comprising the steps of: (a) liquefaction of the raw materials in the presence of an alpha-amylase for obtaining liquefied mash; (b) saccharification of the liquefied mash in the presence of a glucoamylase for obtaining hydrolyzed starch and sugars; (c) fermentation of the hydrolyzed starch and sugars by yeast for obtaining ethanol; (d) recovering alcohol; wherein a protease is introduced in the liquefied mash during the saccharification and/or in the hydrolyze starch and sugars during the fermentation. The yeast advantageously has an increased rate and yield of ethanol production, presumably as a result of increased availability of energy for the yeast's consumption.

According to U.S. Pat. No. 5,231,017, acid fungal protease may be derived from *Aspergillus, Mucor, Rhizopus, Candida, Coriolus, Endothia, Enthomophtora, Irpex, Penicillium, Sclerotium* and *Torulopsis*. In embodiments, the acid fungal protease chosen is thermally stable and is derived from *Aspergillus*, such as *A. niger, A. saitoi* or *A. oryzae*, from *Mucor* such as *M. pusillus* or *M. miehei*, from *Endothia*, such as *E. parasitica*, or from *Rhizopus*. Most preferably, the acid fungal protease is derived from *Aspergillus niger* (for example, one acid fungal protease from *Aspergillus niger*, var. is available under the trade mark AFP-2000 through Solvay Enzymes, Inc.).

The quantity of the acid fungal protease for use in the process herein will depend on the enzymatic activity of the protease, as appreciated by one of skill in the art.

Also available in the art are preparations of glucoamylase and protease blends for simultaneous starch and protein hydrolysis. For example, Fermenzyme L-400 provides a mixture of ~10-15% glucoamylase and <1% protease (Genencor®, Palo Alto, Calif.).

Protease use in ethanol production from dry fractionated corn has been studied (Bernardo, Jr., C. Vidal, Ph.D. Thesis, Univ. of Illinois at Urbana-Champaign, 2010). Of particular note, protease NS50045 (Novozymes, Franklinton, N.C.) treatment was found to result in at least 1% increase in the molar content of all amino acids (except cysteine) in a corn slurry produced from endosperm and germ. For example, a ~9.3% and ~7.5% increase in leucine content was measured after protease treatment of the endosperm and germ, respectively.

Also provided are processes for introducing an effective amount of antioxidant or antioxidant-like compound into an extractant composition used to recover butanol from a fermentation process. The processes comprise (a) providing a fermentation medium comprising a fermentable carbon source, a recombinant microorganism comprising an engineered butanol biosynthetic pathway, and butanol, wherein the fermentable carbon source is provided by processing biomass; (b) contacting said fermentation medium with an extractant composition, whereby the extractant composition does not comprise an effective amount of antioxidant or antioxidant-like compound, and whereby at least a portion of the butanol in the fermentation medium partitions into the extractant; (c) adjusting the amount of antioxidant or antioxidant-like compound in the extractant composition by further processing the biomass with a protease, whereby the protease releases free amino acids from the biomass and whereby the amino acids provide the extractant composition with an effective amount of antioxidant or antioxidant-like compound; (d) recovering at least a portion of the butanol and extractant composition from the fermentation medium; (e) recycling the extractant composition recovered in (d) one or more times to the fermentation medium; and (f) optionally adjusting the effective amount of antioxidant or antioxidant-like compound in the extractant composition whereby the rate of oxidation or the effect of the oxidation products of the recycled extractant composition is substantially reduced and/or avoided such that the extractant composition may be recycled as provided in step (e) for at least ten recycles.

In certain embodiments, the steps of the process can occur contemporaneously. By way of an example, steps (b) and (c) occur contemporaneously. By way of another example, steps (c) and (d) occur contemporaneously. By way of another example, steps (b), (c), and (d) occur contemporaneously.

In certain embodiments, the steps of the process can occur in the same vessel. By way of an example, steps (b) and (c) occur in the same vessel. By way of another example, steps (c) and (d) occur in the same vessel. By way of another example, steps (b), (c), and (d) occur in the same vessel. The vessel can, for example, be a fermentation vessel.

The protease can, for example, be deactivated at a temperature of at least about 85° C. for at least about 15 minutes. Optionally, the protease is a universal protease capable of hydrolyzing between any amino acid bonds in a polypeptide. Examples of universal proteases can include, but are not limited to, Pronase®, Fermgen®, and Flavourzyme®. Universal proteases are known in the art.

Also provided are processes for preventing or reducing the oxidation rate of a recycled extractant or the effect of oxidation products on a recycled extractant. The processes comprise (a) providing a fermentation medium comprising a fermentable carbon source, a recombinant microorganism comprising an engineered butanol biosynthetic pathway, and butanol; (b) contacting said fermentation medium with an extractant composition comprising an effective amount of antioxidant or antioxidant-like compound, whereby at least a portion of the butanol in the fermentation medium partitions into the extractant; (c) recovering at least a portion of the butanol and extractant composition from the fermentation medium; (d) adding antioxidants or antioxidant-like compounds to the extractant composition recovered in (c); and (e) recycling the extractant composition of step (d) one or more times in the fermentation medium.

Also provided are methods for maintaining the oxidative state of an extractant composition during a butanol fermentation process. The methods comprise (a) providing a fermentation medium comprising a fermentable carbon source, a recombinant microorganism comprising an engineered butanol biosynthetic pathway, and butanol; (b) contacting said fermentation medium with an extractant composition comprising an effective amount of antioxidant or antioxidant-like compound, whereby at least a portion of the butanol in the fermentation medium partitions into the extractant; (c) recovering at least a portion of the butanol and extractant composition from the fermentation medium; (d) monitoring one or more of the antioxidative activity index, effective rate, titer, yield of butanol production or the growth of the recombinant microorganism during fermentation; (e) supplementing the extractant composition with antioxidant or antioxidant-like compound following step (d) when said monitoring indicates a decrease in the antioxidative activity index or a toxicity to the recombinant microorganism.

Also provided are methods for optimizing extraction of butanol from a butanol fermentation. The methods comprise (a) providing a fermentation medium comprising a fermentable carbon source, a recombinant microorganism comprising an engineered butanol biosynthetic pathway, and butanol; (b) providing an extractant composition comprising an effective amount of antioxidant or antioxidant-like compound, butanol and free fatty acids, wherein the antioxidant or antioxidant-like compound is produced by the recombinant microorganism during fermentation; and (c) contacting the fermentation medium of (a) with the extractant composition of (b) whereby the butanol partitions into the extractant composition and is distilled from the extractant. Optionally, the methods further comprise recycling the extractant composition of (c) after the butanol is distilled.

Also provided are methods for improving the yield of an isobutanol fermentation. The methods comprise (a) providing a fermentation medium comprising a fermentable carbon source, a recombinant microorganism comprising an engineered isobutanol biosynthetic pathway, and isobutanol; (b) providing an extractant composition comprising an effective amount of antioxidant or antioxidant-like compound, isobutanol and free fatty acids; and (c) contacting the fermentation medium of (a) with the extractant composition of (b) whereby isobutanol partitions into the extractant composition, wherein the yield of isobutanol is improved as compared to yield of isobutanol in the absence of the antioxidant or antioxidant-like compound.

Also provided are methods for improving the titer of isobutanol produced during a fermentation process. The methods comprise (a) providing a fermentation medium comprising a fermentable carbon source, a recombinant microorganism comprising an engineered isobutanol biosynthetic pathway, and isobutanol; (b) providing an extractant composition comprising an effective amount of antioxidant or antioxidant-like compound, isobutanol and free fatty acids; and (c) contacting the fermentation medium of (a) with the extractant composition of (b) whereby isobutanol partitions into the extractant composition, wherein the titer of isobutanol production is improved as compared to titer of isobutanol production in the absence of the antioxidant or antioxidant-like compound.

Also provided are methods for improving the rate of an isobutanol production during a fermentation process. The methods comprise (a) providing a fermentation medium comprising a fermentable carbon source, a recombinant microorganism comprising an engineered isobutanol biosynthetic pathway, and isobutanol; (b) providing an extractant composition comprising an effective amount of antioxidant or antioxidant-like compound, isobutanol and free fatty acids; and (c) contacting the fermentation medium of (a) with the extractant composition of (b) whereby the isobutanol partitions into the extractant composition, wherein the rate of isobutanol production is improved as compared to rate of isobutanol production in the absence of the antioxidant or antioxidant-like compound.

Also provided are methods for increasing the levels of butanol partitioning into an extractant composition in a butanol fermentation process. The methods comprise (a) providing a fermentation medium comprising a fermentable carbon source, a recombinant microorganism comprising a butanol biosynthetic pathway, and butanol; (b) providing an extractant composition comprising an effective amount of antioxidant or antioxidant-like compound, wherein the antioxidant or antioxidant like compound increases the butanol partition coefficient of the extractant; and (c) contacting the fermentation medium of (a) with the extractant composition of (b) whereby increased levels of butanol partition into the extractant composition as compared to the levels of butanol partitioning in an extractant composition that does not comprise an effective amount of antioxidant or antioxidant-like compound or an extractant composition that does not comprise an antioxidant or antioxidant like compound that increases the butanol partition coefficient of the extractant.

Also provided are methods for reducing microbial contamination in a butanol fermentation process. The methods comprise (a) providing a fermentation medium comprising a fermentable carbon source, a recombinant microorganism comprising a butanol biosynthetic pathway, and butanol; (b) providing an extractant composition comprising an effective amount of antioxidant or antioxidant-like compound, wherein the antioxidant or antioxidant-like compound comprises antimicrobial activity; and (c) contacting the fermentation medium of (a) with the extractant composition of (b) whereby microbial contamination of a butanol fermentation is reduced as compared to a butanol fermentation utilizing an extractant composition that does not comprise an effective amount of antioxidant or antioxidant-like compound or an extractant composition that does not comprise an antioxidant or antioxidant-like compound with antimicrobial activity.

Further provided are biphasic compositions. The biphasic compositions can comprise (a) a first phase comprising a fermentation medium comprising a fermentable carbon source, a recombinant microorganism comprising an engineered biosynthetic pathway for producing a product alcohol, and a product alcohol; and (b) a second phase comprising an extractant composition comprising an effective amount of antioxidant or antioxidant-like compound, product alcohol, and free fatty acids, wherein the free fatty acids and antioxidant or antioxidant-like compound are derived from the fermentable carbon source. Optionally, the engineered biosynthetic pathway is a butanol biosynthetic pathway and the product alcohol is butanol.

Optionally, an extractant composition comprising an effective amount of antioxidant has an antioxidant activity index of at least about 1.1. The antioxidative activity index of the extractant composition may be at least about 1.1 to about 15, at least about 2 to about 12, or at least about 5 to about 10. The antioxidative activity index of the extractant composition may be about 1.1, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15.

Optionally, the extractant is selected from the group consisting of corn oil fatty acid (COFA), soy oil fatty acid (SOFA), castor oil fatty acid, oleyl alcohol, COFA based fatty acid methyl esters (FAME), SOFA based FAME, fatty acid butyl esters (FABE), and mixtures thereof.

Recombinant Microorganisms

While not wishing to be bound by theory, it is believed that the processes described herein are useful in conjunction with any alcohol producing microorganism, particularly recombinant microorganisms which produce alcohol.

Recombinant microorganisms which produce alcohol are also known in the art (e.g., Ohta et al., Appl. Environ. Microbiol. 57:893-900 (1991); Underwood et al., Appl. Envrion. Microbiol. 68:1071-81 (2002); Shen and Liao, Metab. Eng. 10:312-20 (2008); Hahnai et al., Appl. Environ. 73:7814-8 (2007); U.S. Pat. No. 5,514,583; U.S. Pat. No. 5,712,133; International Publication No. WO 1995/028476; Feldmann et al., Appl. Microbiol. Biotechnol. 38:354-61 (1992); Zhang et al., Science 267:240-3 (1995); U.S. Patent Publication No. 2007/0031918A1; U.S. Pat. No. 7,223,575; U.S. Pat. No. 7,741,119; U.S. Patent Publication No. 2009/0203099A1; U.S. Patent Publication No. 2009/0246846A1; and International Publication No. WO 2010/075241, which are herein incorporated by reference).

For example, the metabolic pathways of microorganisms may be genetically modified to produce butanol. These pathways may also be modified to reduce or eliminate undesired metabolites, and thereby improve yield of the product alcohol. Optionally, in fermentation processes where oxygen is needed for microorganism growth and butanol production, these pathways can be modified to achieve the proper balance between growth and butanol production of the microorganism and the kinetics of extractant oxidation. By way of an example, the pathways could be modified to increase the growth rate of the microorganism in lower levels or in the absence of oxygen, thereby reducing the kinetics of oxidation of the extractant. The production of butanol by a microorganism is disclosed, for example, in U.S. Pat. Nos. 7,851,188; 7,993,889; 8,178,328, 8,206,970; U.S. Patent Application Publication Nos. 2007/0292927; 2008/0182308; 2008/

0274525; 2009/0305363; 2009/0305370; 2011/0250610; 2011/0313206; and 2011/0111472, the entire contents of each are herein incorporated by reference. In some embodiments, microorganisms comprise a butanol biosynthetic pathway or a biosynthetic pathway for a butanol isomer such as 1-butanol, 2-butanol, or isobutanol. In some embodiments, the biosynthetic pathway converts pyruvate to a fermentative product. In some embodiments, the biosynthetic pathway converts pyruvate as well as amino acids to a fermentative product. In some embodiments, at least one, at least two, at least three, at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism.

In some embodiments, the microorganism may be bacteria, cyanobacteria, filamentous fungi, or yeasts. Suitable microorganisms capable of producing product alcohol (e.g., butanol) via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Lactococcus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma,* or *Saccharomyces*. In one embodiment, recombinant microorganisms may be selected from the group consisting of *Escherichia coli, Alcaligenes eutrophus, Bacillus licheniformis, Paenibacillus macerans, Rhodocuccus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluveromyces thermotolerans, Issatchenkia orientalis, Debaryomyces hansenii,* and *Saccharomyces cerevisiae*. In one embodiment, the genetically modified microorganism is yeast. In one embodiment, the genetically modified microorganism is a crabtree-positive yeast selected from *Saccharomyces, Zygosaccharomyces, Schizosaccharomyces, Dekkera, Torulopsis, Brettanomyces,* and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Zygosaccharomyces rouxii, Zygosaccharomyces bailli,* and *Candida glabrata*.

In some embodiments, the host cell is *Saccharomyces cerevisiae*. *Saccharomyces cerevisiae* are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, and tolerance to product alcohol. In addition, immobilization and encapsulation may minimize the effects of the process conditions such as shearing on the microorganisms.

Biosynthetic pathways for the production of isobutanol that may be used include those as described by Donaldson et al. in U.S. Pat. No. 7,851,188; U.S. Pat. No. 7,993,388; and International Publication No. WO 2007/050671, which are incorporated herein by reference. In one embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by acetohydroxy acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to isobutyraldehyde, which may be catalyzed, for example, by a branched-chain α-keto acid decarboxylase; and, e) the isobutyraldehyde from step d) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to a-ketoisovalerate, which may be catalyzed, for example, by dihydroxy-acid dehydratase;

d) the α-ketoisovalerate from step c) to valine, which may be catalyzed, for example, by transaminase or valine dehydrogenase;

e) the valine from step d) to isobutylamine, which may be catalyzed, for example, by valine decarboxylase;

f) the isobutylamine from step e) to isobutyraldehyde, which may be catalyzed by, for example, omega transaminase; and, g) the isobutyraldehyde from step f) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by acetohydroxy acid reductoisomerase;

c) the 2,3-dihydroxyisovalerate from step b) to α-ketoisovalerate, which may be catalyzed, for example, by acetohydroxy acid dehydratase;

d) the α-ketoisovalerate from step c) to isobutyryl-CoA, which may be catalyzed, for example, by branched-chain keto acid dehydrogenase;

e) the isobutyryl-CoA from step d) to isobutyraldehyde, which may be catalyzed, for example, by acylating aldehyde dehydrogenase; and, f) the isobutyraldehyde from step e) to isobutanol, which may be catalyzed, for example, by a branched-chain alcohol dehydrogenase.

Biosynthetic pathways for the production of 1-butanol that may be used include those described in U.S. Patent Application Publication No. 2008/0182308 and WO2007/041269, which are incorporated herein by reference. In one embodiment, the 1-butanol biosynthetic pathway comprises the following substrate to product conversions:

a) acetyl-CoA to acetoacetyl-CoA, which may be catalyzed, for example, by acetyl-CoA acetyltransferase;

b) the acetoacetyl-CoA from step a) to 3-hydroxybutyryl-CoA, which may be catalyzed, for example, by 3-hydroxybutyryl-CoA dehydrogenase;

c) the 3-hydroxybutyryl-CoA from step b) to crotonyl-CoA, which may be catalyzed, for example, by crotonase;

d) the crotonyl-CoA from step c) to butyryl-CoA, which may be catalyzed, for example, by butyryl-CoA dehydrogenase;

e) the butyryl-CoA from step d) to butyraldehyde, which may be catalyzed, for example, by butyraldehyde dehydrogenase; and, f) the butyraldehyde from step e) to 1-butanol, which may be catalyzed, for example, by butanol dehydrogenase.

Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In one embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetonin aminase;

d) the 3-amino-2-butanol from step c) to 3-amino-2-butanol phosphate, which may be catalyzed, for example, by aminobutanol kinase;

e) the 3-amino-2-butanol phosphate from step d) to 2-butanone, which may be catalyzed, for example, by aminobutanol phosphate phosphorylase; and, f) the 2-butanone from step e) to 2-butanol, which may be catalyzed, for example, by butanol dehydrogenase.

In another embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin to 2,3-butanediol from step b), which may be catalyzed, for example, by butanediol dehydrogenase;

d) the 2,3-butanediol from step c) to 2-butanone, which may be catalyzed, for example, by dial dehydratase; and, e) the 2-butanone from step d) to 2-butanol, which may be catalyzed, for example, by butanol dehydrogenase.

Biosynthetic pathways for the production of 2-butanone that may be used include those described in U.S. Pat. No. 8,206,970 and U.S. Patent Application Publication Nos. 2007/0292927 and 2009/0155870, which are incorporated herein by reference. In one embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetonin aminase;

d) the 3-amino-2-butanol from step c) to 3-amino-2-butanol phosphate, which may be catalyzed, for example, by aminobutanol kinase; and, e) the 3-amino-2-butanol phosphate from step d) to 2-butanone, which may be catalyzed, for example, by aminobutanol phosphate phosphorylase.

In another embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin which may be catalyzed, for example, by acetolactate decarboxylase;

c) the acetoin from step b) to 2,3-butanediol, which may be catalyzed, for example, by butanediol dehydrogenase;

d) the 2,3-butanediol from step c) to 2-butanone, which may be catalyzed, for example, by diol dehydratase.

Organic Extractants

Extractants useful in the methods described herein are water immiscible organic solvents. Suitable organic extractants should meet the criteria for an ideal solvent for a commercial two-phase extractive fermentation for the production or recovery of butanol. Specifically, the extractant should (i) be nontoxic to the butanol-producing microorganisms such as, for example, the recombinant microorganisms described herein, (ii) be substantially immiscible with the fermentation medium, (iii) have a high partition coefficient for the extraction of butanol, (iv) have a low partition coefficient for the extraction of nutrients, (v) have a low tendency to form emulsions with the fermentation medium, and (vi) be low cost and nonhazardous. Suitable organic extractants for use in the methods disclosed herein are selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes and mixtures thereof. As used herein, the term "mixtures thereof" encompasses both mixtures within and mixtures between these group members, for example mixtures within $C_{12}$ to $C_{22}$ fatty alcohols, and also mixtures between $C_{12}$ to $C_{22}$ fatty alcohols and $C_{12}$ to $C_{22}$ fatty acids, for example.

Suitable organic extractants are further selected from the group consisting of oleyl alcohol (CAS No. 143-28-2), behenyl alcohol (CAS No. 661-19-8), cetyl alcohol (CAS No. 36653-82-4), lauryl alcohol, also referred to as 1-dodecanol (CAS No. 112-53-8), myristyl alcohol (112-72-1), stearyl alcohol (CAS No. 112-92-5), 1-undecanol (CAS No. 112-42-5), oleic acid (CAS No. 112-80-1), lauric acid (CAS No. 143-07-7), myristic acid (CAS No. 544-63-8), stearic acid (CAS No. 57-11-4), methyl myristate CAS No. 124-10-7), methyl oleate (CAS No. 112-62-9), undecanal (CAS No. 112-44-7), lauric aldehyde (CAS No. 112-54-9), 20-methylundecanal (CAS No. 110-41-8), and mixtures thereof. These organic extractants are available commercially from various sources, such as Sigma-Aldrich (St. Louis, Mo.), in various grades, many of which may be suitable for use in extractive fermentation to produce or recover butanol. Technical grades contain a mixture of compounds, including the desired component and higher and lower fatty components. For example, one commercially available technical grade oleyl alcohol contains about 65% oleyl alcohol and a mixture of higher and lower fatty alcohols.

In certain embodiments, the extractant can be one or more of the following fatty acids: azaleic, capric, caprylic, castor, coconut (i.e., as a naturally-occurring combination of fatty acids, including lauric, myrisitic, palmitic, caprylic, capric, stearic, caproic, arachidic, oleic, and linoleic, for example), dimer, isostearic, lauric, linseed, myristic, oleic, olive, palm oil, palmitic, palm kernel, peanut, pelargonic, ricinoleic, sebacic, soya, stearic acid, tall oil, tallow, #12 hydroxy stearic, or any seed oil. In some embodiments, the extractant can be one or more of diacids, azaleic, dimer and sebacic acid. Thus, in some embodiments, the extractant can be a mixture of two or more different fatty acids. In some embodiments, the extractant can be a fatty acid derived from chemical or enzymatic hydrolysis of glycerides derived from native oil. For example, in some embodiments, the extractant can be free fatty acids obtained by enzymatic hydrolysis of native oil such as biomass lipids. In some embodiments, the extractant can be a fatty acid extractant selected from the group consisting of fatty acids, fatty alcohols, fatty amides, fatty acid methyl esters, lower alcohol esters of fatty acids, fatty acid glycol esters, hydroxylated triglycerides, and mixtures thereof, obtained from chemical conversion of native oil such as biomass lipids as described in U.S. Patent Publication No. 2011/0312044. In such embodiments, the biomass lipids for producing extractant can be from a same or different biomass source from which feedstock is obtained. For example, in some embodiments, the biomass lipids for producing extractant can be derived from soya, whereas the biomass source of feedstock is corn. Any possible combination of different biomass sources for extractant versus feedstock can be used, as should be apparent to one of skill in the art. In some embodiments, additional extractant includes COFA.

One of reasonable skill in the art can appreciate that it may be advantageous to use a mixture of the organic extractants. For example, solvent mixtures may be used to increase the partition coefficient of the product. Additionally, solvent mixtures may be used to adjust and optimize physical characteristics of the solvent, such as the density, boiling point, and viscosity.

Growth for Production

Recombinant host cells disclosed herein are contacted with suitable carbon substrates, typically in fermentation media. Additional carbon substrates may include, but are not limited to, monosaccharides such as fructose, oligosaccharides such as lactose, maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [Int. Symp.], 7$^{th}$ (1993), 415-32, Editors: Murrell, J. Collin, Kelly, Don P.; Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. 2007/0031918 A1, which is herein incorporated by reference. Biomass, when used in reference to carbon substrate, refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway described herein.

In some embodiments, the butanologen produces butanol at least 90% of effective yield, at least 91% of effective yield, at least 92% of effective yield, at least 93% of effective yield, at least 94% of effective yield, at least 95% of effective yield, at least 96% of effective yield, at least 97% of effective yield, at least 98% of effective yield, or at least 99% of effective yield. In some embodiments, the butanologen produces butanol at about 55% to at about 75% of effective yield, about 50% to about 80% of effective yield, about 45% to about 85% of effective yield, about 40% to about 90% of effective yield, about 35% to about 95% of effective yield, about 30% to about 99% of effective yield, about 25% to about 99% of effective yield, about 10% to about 99% of effective yield, or about 10% to about 100% of effective yield.

Culture Conditions

Typically cells are grown at a temperature in the range of about 20° C. to about 40° C. in an appropriate medium. In some embodiments, the cells are grown at a temperature of 20° C., 22° C., 25° C., 27° C., 30° C., 32° C., 35° C., 37° C. or 40° C. In some embodiments, the cells are grown at a temperature of about 25° C. to about 40° C. in an appropriate medium. Suitable growth media in the present invention are common commercially prepared media such as Luria Bertani (LB) broth, Sabouraud Dextrose (SD) broth or Yeast Medium (YM) broth or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), can also be incorporated into the fermentation medium.

Suitable pH ranges for the fermentation are between pH 5.0 to pH 9.0, where pH 6.0 to pH 8.0 is preferred for the initial condition. Suitable pH ranges for the fermentation of yeast are typically between about pH 3.0 to about pH 9.0. In one embodiment, about pH 5.0 to about pH 8.0 is used for the initial condition. Suitable pH ranges for the fermentation of other microorganisms are between about pH 3.0 to about pH 7.5. In one embodiment, about pH 4.5 to about pH 6.5 is used for the initial condition.

Fermentations can be performed under aerobic or anaerobic conditions. In one embodiment, anaerobic or microaerobic conditions are used for fermentation.

In some embodiments, the culture conditions are such that the fermentation occurs without respiration. For example, cells can be cultured in a fermenter under micro-aerobic or anaerobic conditions.

Methods for Producing Butanol Using Two-Phase Extractive Fermentation

The microorganism may be cultured in a suitable fermentation medium in a suitable fermentor to produce butanol. Any suitable fermentor may be used including a stirred tank fermentor, an airlift fermentor, a bubble fermentor, or any combination thereof. Materials and methods for the maintenance and growth of microbial cultures are well known to those skilled in the art of microbiology or fermentation science (See for example, Bailey et al., *Biochemical Engineering Fundamentals*, second edition, McGraw Hill, New York, 1986). Consideration must be given to appropriate fermentation medium, pH, temperature, and requirements for aerobic, microaerobic, or anaerobic conditions, depending on the specific requirements of the microorganism, the fermentation, and the process. The fermentation medium used is not critical, but it must support growth of the microorganism used and promote the biosynthetic pathway necessary to produce the desired butanol product. A conventional fermentation medium may be used, including, but not limited to, complex media containing organic nitrogen sources such as yeast extract or peptone and at least one fermentable carbon source; minimal media; and defined media. Suitable fermentable carbon sources include, but are not limited to, monosaccharides, such as glucose or fructose; disaccharides, such as lactose or sucrose; oligosaccharides; polysaccharides, such as starch or cellulose; one carbon substrates; amino acids; and mixtures thereof. In addition to the appropriate carbon source, the fermentation medium may contain a suitable nitrogen source, such as an ammonium salt, yeast extract or peptone, minerals, salts, cofactors, buffers and other components, known to those skilled in the art (Bailey et al. supra). Suitable conditions for the extractive fermentation depend on the particular microorganism used and may be readily determined by one skilled in the art using routine experimentation.

Methods for Recovering Butanol Using Extractive Fermentation

Butanol may be recovered from a fermentation medium containing butanol, water, at least one fermentable carbon source, and a recombinant microorganism that has been genetically modified (that is, genetically engineered) to produce butanol via an engineered biosynthetic pathway from at least one carbon source. Such genetically modified microorganisms can be selected from the group disclosed above. The first step in the process is contacting the fermentation medium with a water immiscible organic extractant, described above, to form a two-phase mixture comprising an aqueous phase and a butanol-containing organic phase. "Contacting" means the fermentation medium and the organic extractant are brought into physical contact at any time during the fermentation process.

The organic extractant may contact the fermentation medium at the start of the fermentation forming a biphasic fermentation medium. Alternatively, the organic extractant may contact the fermentation medium after the microorganism has achieved a desired amount of growth, which can be determined by measuring the optical density of the culture.

Further, the organic extractant may contact the fermentation medium at a time at which the butanol level in the fermentation medium reaches a preselected level, for example, before the butanol concentration reaches a toxic level. The butanol concentration may be monitored during the fermentation using methods known in the art, such as gas chromatography or high performance liquid chromatography.

The fermentation may be run under aerobic conditions for a time sufficient for the culture to achieve a preselected level of growth, which may be determined by optical density measurement. After the preselected level of growth is achieved, the fermentation conditions may be switched to microaerobic or anaerobic conditions. Switching the fermentation conditions to microaerobic or anaerobic conditions can, for example, reduce the level of oxidation of the extractant.

The fermentation medium is contacted with the organic extractant, and the butanol product partitions into the organic extractant, decreasing the concentration in the aqueous phase, thereby limiting the exposure of the production microorganism to the inhibitory butanol product. The volume of the organic extractant to be used depends on a number of factors, including the volume of the fermentation medium, the size of the fermentor, the partition coefficient of the extractant for the butanol product, and the fermentation mode. In embodiments, the volume of the organic extractant is about 3% to about 60% of the fermentor working volume. The contact with the organic extractant may occur within the fermentation vessel, but may occur in a separate vessel downstream of the fermentation vessel.

Recovery of the butanol from the butanol-containing organic phase can be done using methods known in the art, including but not limited to, distillation, adsorption by resins, separation by molecular sieves, pervaporation, and the like. Specifically, distillation may be used to recover the butanol from the butanol-containing organic phase.

Any butanol remaining in the fermentation medium after the fermentation run is completed may be recovered by continued extraction using fresh or recycled organic extractant. The fresh or recycled organic extractant can be supplemented with antioxidants or antioxidant-like compounds. Alternatively, the butanol can be recovered from the fermentation medium using methods known in the art, such as distillation, azeotropic distillation, liquid-liquid extraction, adsorption, gas stripping, membrane evaporation, pervaporation, and the like.

The two-phase extractive fermentation method may be carried out in a continuous mode in a stirred tank fermentor. In this mode, the mixture of the fermentation medium and the butanol-containing organic extractant is removed from the fermentor. The two phases are separated by means known in the art including, but not limited to, siphoning, decantation, centrifugation, using a gravity settler, membrane-assisted phase splitting, and the like, as described above. After separation, the fermentation medium may be recycled to the fermentor or may be replaced with fresh medium. Then, the extractant is treated to recover the butanol product as described above. The extractant may then be recycled back into the fermentor for further extraction of the product. Alternatively, fresh extractant may be continuously added to the fermentor to replace the removed extractant. This continuous mode of operation offers several advantages. Because the product is continually removed from the reactor, a smaller volume of organic extractant is required enabling a larger volume of the fermentation medium to be used. This results in higher production yields. The volume of the organic extractant may be about 3% to about 50% of the fermentor working volume; 3% to about 20% of the fermentor working volume; or 3% to about 10% of the fermentor working volume. It is beneficial to use the smallest amount of extractant in the fermentor as possible to maximize the volume of the aqueous phase, and therefore, the amount of cells in the fermentor. The process may be operated in an entirely continuous mode in which the extractant is continuously recycled between the fermentor and a separation apparatus and the fermentation medium is continuously removed from the fermentor and replenished with fresh medium. In this entirely continuous mode, the butanol product is not allowed to reach the critical toxic concentration and fresh nutrients are continuously provided so that the fermentation may be carried out for long periods of time. Optionally, the extractant can be supplemented with antioxidants or antioxidant-like compounds in the event that recycling of the extractant results in oxidation of the extractant. The apparatus that may be used to carry out these modes of two-phase extractive fermentations are well known in the art. Examples are described, for example, by Kollerup et al. in U.S. Pat. No. 4,865,973.

Batchwise fermentation mode may also be used. Batch fermentation, which is well known in the art, is a closed system in which the composition of the fermentation medium is set at the beginning of the fermentation and is not subjected to artificial alterations during the process. In this mode, a volume of organic extractant is added to the fermentor and the extractant is not removed during the process. Although this mode is simpler than the continuous or the entirely continuous modes described above, it requires a larger volume of organic extractant to minimize the concentration of the inhibitory butanol product in the fermentation medium. Consequently, the volume of the fermentation medium is less and the amount of product produced is less than that obtained using the continuous mode. The volume of the organic solvent in the batchwise mode may be 20% to about 60% of the fermentor working volume; or 30% to about 60% of the fermentor working volume. It is beneficial to use the smallest volume of extractant in the fermentor as possible in the event that the extractant is oxidized, at least because a lower level of antioxidants or antioxidant-like compounds will need to added to the recycled extractant to restore or increase the antioxidant capability of the extractant.

Fed-batch fermentation mode may also be used. Fed-batch fermentation is a variation of the standard batch system, in which the nutrients, for example glucose, are added in increments during the fermentation. The amount and the rate of addition of the nutrient may be determined by routine experimentation. For example, the concentration of critical nutrients in the fermentation medium may be monitored during the fermentation. Alternatively, more easily measured factors such as pH, dissolved oxygen, and the partial pressure of waste gases, such as carbon dioxide, may be monitored. From these measured parameters, the rate of nutrient addition may be determined. The amount of organic solvent used in this mode is the same as that used in the batch-wise mode, described above.

Extraction of the product may be done downstream of the fermentor, rather than in situ. In this mode, the extraction of the butanol product into the organic extractant is carried out on the fermentation medium removed from the fermentor. The amount of organic solvent used is about 20% to about 60% of the fermentor working volume; or 30% to about 60% of the fermentor working volume. The fermentation medium may be removed from the fermentor continuously or periodically, and the extraction of the butanol product by the organic extractant may be done with or without the removal of the cells from the fermentation medium. The cells may be removed from the fermentation medium by means known in the art including, but not limited to, filtration or centrifugation. After separation of the fermentation medium from the extractant by means described above, the fermentation medium may be recycled into the fermentor, discarded, or treated for the removal of any remaining butanol product. Similarly, the isolated cells may also be recycled into the fermentor. After treatment to recover the butanol product, the extractant may be recycled for use in the extraction process. Alternatively, fresh extractant may be used. In this mode the solvent is not present in the fermentor, so the toxicity of the solvent is much less of a problem. If the cells are separated from the fermentation medium before contacting with the solvent, the problem of solvent toxicity is further reduced. Furthermore, using this mode there is less chance of forming an emulsion and evaporation of the solvent is minimized, alleviating environmental concerns.

A method for the production of butanol is provided, wherein a microorganism that has been genetically modified of being capable of converting at least one fermentable carbon source into butanol, is grown in a biphasic fermentation medium. The biphasic fermentation medium comprises an aqueous phase and a water immiscible organic extractant, as described above, wherein the biphasic fermentation medium comprises from about 3% to about 60% by volume of the organic extractant. The microorganism may be grown in the biphasic fermentation medium for a time sufficient to extract butanol into the extractant to form a butanol-containing organic phase. In the case where the fermentation medium further comprises ethanol, the butanol-containing organic phase may contain ethanol. The butanol-containing organic phase is then separated from the aqueous phase, as described above. Subsequently, the butanol is recovered from the butanol-containing organic phase, as described above.

Referring now to FIG. 5, there is shown a schematic representation of one embodiment of processes for producing and recovering butanol using in situ extractive fermentation. An aqueous stream 10 of at least one fermentable carbon source is introduced into a fermentor 20, which contains at least one microorganism (not shown) genetically modified to convert the at least one fermentable carbon source into butanol. A stream of the first water immiscible extractant 12 and a stream of the optional second water immiscible extractant 14 are introduced to a vessel 16, in which the extractants are combined to form the extractant 18. A stream of the extractant 18 is introduced into the fermentor 20, whereby contact between the fermentation medium and the extractant to form a two-phase mixture comprising an aqueous phase and a butanol-containing organic phase occurs. Upon recycling of the extractant, in the event that the extractant comprises diminished antioxidant capabilities, the extractant can be supplemented with antioxidants or antioxidant-like compounds or fresh extractant comprising antioxidant or antioxidant-like capability prior to or concurrently with the stream introduced into the fermentor. A stream 26 comprising both the aqueous and organic phases is introduced into a vessel 38, in which separation of the aqueous and organic phases is performed to produce a butanol-containing organic phase 40 and an aqueous phase 42.

Referring now to FIG. 6, there is shown a schematic representation of one embodiment of processes for producing and recovering butanol using in situ extractive fermentation. An aqueous stream 10 of at least one fermentable carbon source is introduced into a fermentor 20, which contains at least one microorganism (not shown) genetically modified to convert the at least one fermentable carbon source into butanol. A stream of the first water immiscible extractant 12 and a stream of the optional second water immiscible extractant 14 are introduced separately to the fermentor 20, whereby contact between the fermentation medium and the extractant to form a two-phase mixture comprising an aqueous phase and a butanol-containing organic phase occurs. Upon recycling of the extractant, in the event that the extractant comprises diminished antioxidant capabilities, either the first, second, or both water immiscible extractants can be supplemented with antioxidants or antioxidant-like compounds or fresh extractant comprising antioxidant or antioxidant-like capability prior to or concurrently with the stream introduced into the fermentor. A stream 26 comprising both the aqueous and organic phases is introduced into a vessel 38, in which separation of the aqueous and organic phases is performed to produce a butanol-containing organic phase 40 and an aqueous phase 42.

Referring now to FIG. 7, there is shown a schematic representation of one embodiment of processes for producing and recovering butanol using in situ extractive fermentation. An aqueous stream 10 of at least one fermentable carbon source is introduced into a first fermentor 20, which contains at least one microorganism (not shown) genetically modified to convert the at least one fermentable carbon source into butanol. A stream of the first water immiscible extractant 12 is introduced to the fermentor 20, and a stream 22 comprising a mixture of the first solvent and the contents of fermentor 20 is introduced into a second fermentor 24. A stream of the optional second water immiscible extractant 14 is introduced into the second fermentor 24, whereby contact between the fermentation medium and the extractant to form a two-phase mixture comprising an aqueous phase and a butanol-containing organic phase occurs. Upon recycling of the extractant, in the event that the extractant comprises diminished antioxidant capabilities, either the first, second, or both water immiscible extractants can be supplemented with antioxidants or antioxidant-like compounds or fresh extractant comprising antioxidant or antioxidant-like capability prior to or concurrently with the stream introduced into the fermentor. A stream 26 comprising both the aqueous and organic phases is introduced into a vessel 38, in which separation of the aqueous and organic phases is performed to produce a butanol-containing organic phase 40 and an aqueous phase 42.

Referring now to FIG. 8, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one microorganism (not shown) genetically modified to convert the at least one fermentable carbon source into butanol. A stream of the first water immiscible extractant 112 and a stream of the optional second water immiscible extractant 114 are introduced to a vessel 116, in which the water immiscible extractants are combined to form the extractant 118. At least a portion, shown as stream 122, of the fermentation medium in fermentor 120 is introduced into vessel 124. A stream of the extractant 118 is also introduced into vessel 124, whereby contact between the fermentation medium and the extractant to form a two-phase mixture comprising an aqueous phase and a butanol-containing organic phase occurs. Upon recycling of the extractant, in the event that the extractant comprises diminished antioxidant capabilities, either the first, second, or both water immiscible extractants can be supplemented with antioxidants or antioxidant-like compounds or fresh extractant comprising antioxidant or antioxidant-like capability prior to or concurrently with the stream introduced into the fermentor. A stream 126 comprising both the aqueous and organic phases is introduced into a vessel 138, in which separation of the aqueous and organic phases is performed to produce a butanol-containing organic phase 140 and an aqueous phase 142.

Referring now to FIG. 9, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one microorganism (not shown) genetically modified to convert the at least one fermentable carbon source into butanol. A stream of the first water immiscible extractant 112 and a stream of the optional second water immiscible extractant 114 are introduced separately to a vessel 124, in which the water immiscible extractants are combined to form the extractant 118. At least a portion, shown as stream 122, of the fermentation medium in fermentor 120 is also introduced into vessel 124, whereby contact between the fermentation medium and the extractant to form a two-phase mixture comprising an aqueous phase and a butanol-containing organic phase occurs. Upon recycling of the extractant, in the event that the extractant comprises diminished antioxidant capabilities, either the first, second, or both water immiscible extractants can be supplemented with antioxidants or antioxidant-like compounds or fresh extractant comprising antioxidant or antioxidant-like capability prior to or concurrently with the stream introduced into the fermentor. A stream 126 comprising both the aqueous and organic phases is introduced into a vessel 138, in which separation of the aqueous and organic phases is performed to produce a butanol-containing organic phase 140 and an aqueous phase 142.

Referring now to FIG. 10, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one microorganism (not shown) genetically modified to convert the at least one fermentable carbon source into butanol. A stream of the first water immiscible extractant 112 is introduced to a vessel 128, and at least a portion, shown as stream 122, of the fermentation medium in fermentor 120 is also introduced into vessel 128. A stream 130 comprising a mixture of the first water immiscible extractant and the contents of fermentor 120 is introduced into a second vessel 132. A stream of the optional second water immiscible extractant 114 is introduced into the second vessel 132, whereby contact between the fermentation medium and the extractant to form a two-phase mixture comprising an aqueous phase and a butanol-containing organic phase occurs. Upon recycling of the extractant, in the event that the extractant comprises diminished antioxidant capabilities, either the first, second, or both water immiscible extractants can be supplemented with antioxidants or antioxidant-like compounds or fresh extractant comprising antioxidant or antioxidant-like capability prior to or concurrently with the stream introduced into the fermentor. A stream 134 comprising both the aqueous and organic phases is introduced into a vessel 138, in which separation of the aqueous and organic phases is performed to produce a butanol-containing organic phase 140 and an aqueous phase 142.

The extractive processes described herein can be run as batch processes or can be run in a continuous mode where fresh extractant is added and used extractant is pumped out such that the amount of extractant in the fermentor remains constant during the entire fermentation process. Such continuous extraction of products and byproducts from the fermentation and maintenance of the antioxidant capability of the extractant can increase effective rate, titer and yield.

Methods for Butanol Isolation from the Fermentation Medium

Bioproduced butanol may be isolated from the fermentation medium using methods known in the art for ABE fermentations (see, e.g., Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. The butanol may be isolated from the fermentation medium using methods such as distillation, azeotropic distillation, liquid-liquid extraction, adsorption, gas stripping, membrane evaporation, or pervaporation.

Because butanol forms a low boiling point, azeotropic mixture with water, distillation can be used to separate the mixture up to its azeotropic composition. Distillation may be used in combination with the processes described herein to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see, e.g., Doherty and Malone, *Conceptual Design of Distillation Systems*, McGraw Hill, New York, 2001).

The butanol-water mixture forms a heterogeneous azeotrope so that distillation may be used in combination with decantation to isolate and purify the isobutanol. In this method, the butanol containing fermentation broth is distilled to near the azeotropic composition. Then, the azeotropic mixture is condensed, and the butanol is separated from the fermentation medium by decantation, wherein the butanol can be contacted with an agent to reduce the activity of the one or more carboxylic acids. The decanted aqueous phase may be returned to the first distillation column as reflux or to a separate stripping column. The butanol-rich decanted organic phase may be further purified by distillation in a second distillation column.

The butanol can also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption can also be used to isolate butanol from the fermentation medium. In this method, the fermentation broth containing the butanol is distilled to near the azeotropic composition and then the remaining water is removed by use of an adsorbent, such as molecular sieves (Aden et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation can be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is liquid-liquid extraction. In general, with regard to butanol fermentation, for example, the fermentation medium, which includes the microorganism, is contacted with an organic extractant at a time before the butanol concentration reaches a toxic level. The organic extractant and the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Appl. Pub. Nos. 2009/0305370 and 2011/0097773, the disclosures of which are hereby incorporated in their entirety. U.S. Patent Appl. Pub. Nos. 2009/0305370 and 2011/0097773 describe methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, polyunsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof.

In some embodiments, an alcohol ester can be formed by contacting the alcohol in a fermentation medium with an organic acid (e.g., fatty acids) and a catalyst capable of esterifying the alcohol with the organic acid. In such embodiments, the organic acid can serve as an ISPR extractant into which the alcohol esters partition. The organic acid can be supplied to the fermentation vessel and/or derived from the biomass supplying fermentable carbon fed to the fermentation vessel. Lipids present in the feedstock can be catalytically hydrolyzed to organic acid, and the same catalyst (e.g., enzymes) can esterify the organic acid with the alcohol. Carboxylic acids that are produced during the fermentation can additionally be esterified with the alcohol produced by the same or a different catalyst. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids into organic acid and substantially simultaneous esterification of the organic acid with butanol present in the fermentation vessel. Organic acid and/or native oil not derived from the feedstock can also be fed to the fermentation vessel, with the native oil being hydrolyzed into organic acid. Any organic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to organic acid, thereby decreasing the rate of build-up of lipids in the ISPR extractant.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the organic acid extractant can contact the fermentation medium at a time before the butanol concentration reaches a toxic level, so as to esterify the butanol with the organic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

Confirmation of Isobutanol Production

The presence and/or concentration of isobutanol in the culture medium can be determined by a number of methods known in the art (see, for example, U.S. Pat. No. 7,851,188, incorporated by reference). For example, a specific high performance liquid chromatography (HPLC) method utilizes a Shodex SH-1011 column with a Shodex SHG guard column, both may be purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions used.

Alternatively, gas chromatography (GC) methods are available. For example, a specific GC method utilizes an HP-INNOWax column (30 m×0.53 mm id, 1 µm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature is 45° C. for 1 min, 45 to 220° C. at 10° C./min, and 220° C. for 5 min; and FID detection is employed at 240° C. with 26 mL/min helium makeup gas. The retention time of isobutanol is 4.5 min.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, breadth and scope of the present application should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA, molecular cloning techniques and transformation protocols used in the Examples are well known in the art and are described by Sambrook et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis), by Ausubel et al. (Ausubel et al., Current Protocols in Molecular Biology, pub. by Greene Publishing Assoc. and Wiley-Interscience, 1987) and by Amberg et al (Amberg, D. C., Burke, D. J. and Strathern, J. N. (Methods in Yeast Genetics: A Cold Spring Harbor Laboratory Course Manual, Cold Spring Harbor Press, 2005). Materials and methods suitable for the maintenance and growth of bacterial cultures are well known in the art. Techniques suitable for use in the following examples may be found as set out in Manual of Methods for General Bacteriology (Phillipp et al., eds., American Society for Microbiology, Washington, D.C., 1994) or by Thomas D. Brock in (Brock, Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine chemicals (India), or Takara Bio Inc. (Shiga, Japan), unless otherwise specified.

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "µmole" means micromole(s), "kg" means kilogram, "g" means gram(s), "µg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "µg/L" means microgram per liter, "ng/µL" means nanogram per microliter, "pmol/µL" means picomol per microliter, "RPM" means rotation per minute, "µmol/min/mg" means micromole per minute per milligram, "w/v" means weight per volume, "v/v" means volume per volume.

Example 1

Oxidation Levels of Mixtures of Distilled and Crude Corn Oil Fatty Acid (COFA)

Figure 1:
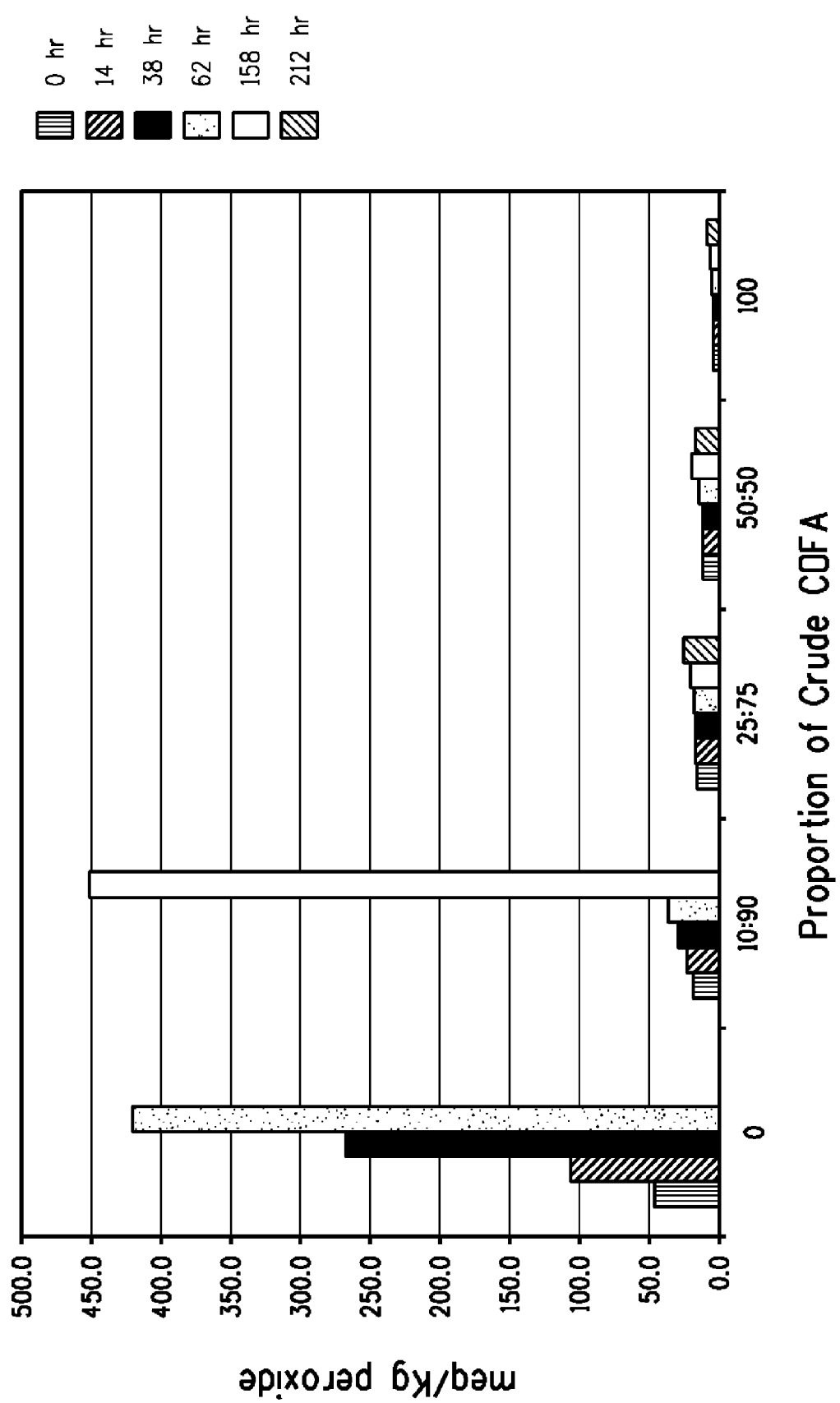
FIG. 1 shows a graph demonstrating the peroxide content of samples of pure (100%) crude corn oil fatty acid (COFA) (100%), pure distilled COFA (100%), and mixtures of crude and distilled COFA (90% distilled/10% crude; 75% distilled/25% crude; and 50% distilled/50% crude) over time.

To determine if crude COFA was capable of rescuing the antioxidant activity of distilled COFA, mixtures of crude and distilled COFA were made and exposed to oxygen for several days at 30° C. 100% crude COFA, 100% distilled COFA, 90% distilled/10% crude COFA, 75% distilled/25% crude COFA, and 50% distilled/50% crude COFA samples were created and exposed to oxygen for several days through slow bubbling of air through neat oil. The peroxide content of the COFA was measured and the results are shown in FIG. 1.

The following samples were prepared from crude COFA prepared as outlined above and distilled COFA (Emery Oleochemicals; Cincinatti, Ohio)

TABLE 1

Composition of samples of crude, distilled, and crude and distilled COFA.

| Sample | Wt Crude COFA | Wt distilled COFA |
|---|---|---|
| A | 20 | 0 |
| B | 0 | 20 |
| C | 2 | 18 |
| D | 5 | 15 |
| E | 10 | 10 |

The samples were put into a heating block held at 30° C. and had air bubbled through the liquid at a rate of 11 ml/min. Samples were removed at indicated times and analyzed for peroxide content and homolog distribution.

At the indicated times aliquots from each sample were taken and analyzed for peroxide content by AOCS method Cd 8-53 with the exception that 0.01N sodium thiosulfate solution is used for the titration instead of 0.1N sodium thiosulfate. The results are shown below in Table 2 and in FIG. 1.

TABLE 2

Peroxide content (meq/Kg) of Samples A-E over time

| Sample-time | Perox-Content |
|---|---|
| A-0 hr | 4.9 |
| A-14 hr | 5.2 |
| A-38 hr | 5.6 |
| A-62 hr | 6.3 |
| A-158 hr | 9.1 |
| A-212 hr | 12.8 |
| B-0 hr | 46.1 |
| B-14 hr | 110.0 |
| B-38 hr | 270.0 |
| B-62 hr | 418.7 |
| C-0 hr | 21.2 |
| C-14 hr | 24.0 |
| C-38 hr | 29.0 |
| C-62 hr | 37.5 |
| C-158 hr | 453.4 |
| D-0 hr | 17.7 |
| D-14 hr | 18.3 |
| D-38 hr | 18.1 |
| D-62 hr | 19.7 |
| D-158 hr | 24.5 |
| D-212 hr | 29.5 |
| E-0 hr | 13.3 |
| E-14 hr | 13.1 |
| E-38 hr | 13.2 |
| E-62 hr | 14.8 |
| E-158 hr | 20.2 |
| E-212 hr | 17.1 |

Figure 2:
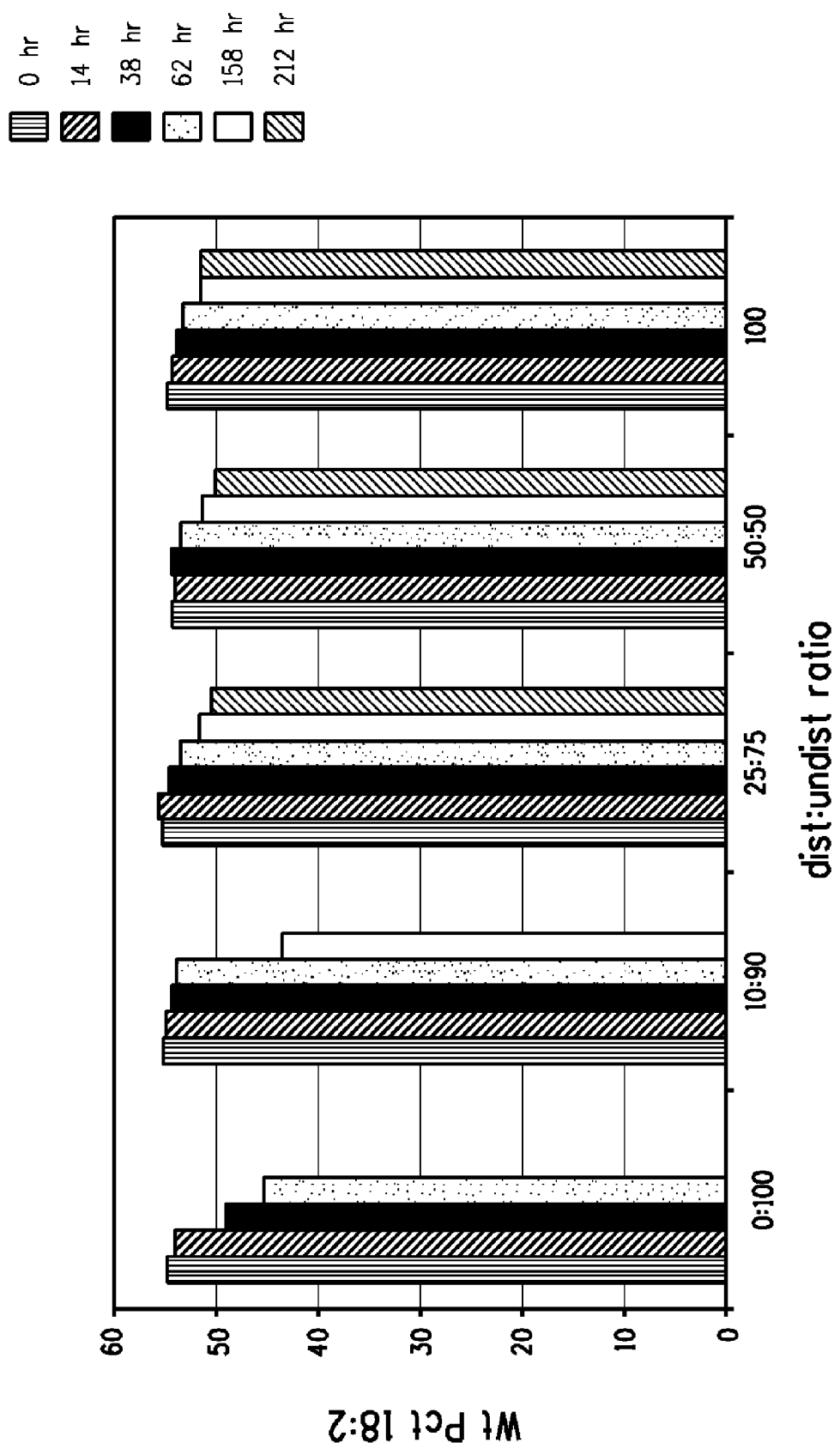
FIG. 2 shows a graph demonstrating the percent of double bonded linoleic acid in pure crude COFA (100%), pure distilled COFA (100%), and mixtures of crude and distilled COFA (90% distilled/10% crude; 75% distilled/25% crude; and 50% distilled/50% crude) over time.

Samples from this experiment were also analyzed by derivatizing the sample to the methyl esters and looking at the gas chromatography (GC) analysis. That data is shown in Table 3 and FIG. 2.

TABLE 3

GC analysis of Samples A-E over time.

| Sample | Name | 16:0 | 18:0 | 18:1 | 18:2 |
|---|---|---|---|---|---|
| A-1 | 0 hr | 11.28 | 1.82 | 23.68 | 54.62 |
| A-2 | 14 hr | 11.21 | 1.8 | 23.48 | 54.12 |
| A-3 | 38 hr | 11.12 | 1.79 | 23.28 | 53.6 |
| A-4 | 62 hr | 10.96 | 1.76 | 22.96 | 52.83 |
| A-5 | 158 hr | 10.76 | 1.73 | 22.54 | 51.94 |
| A-6 | 212 hr | 10.88 | 1.76 | 22.92 | 51.98 |
| B-1 | 0 hr | 9.8 | 2.11 | 26.38 | 54.52 |
| B-2 | 14 hr | 9.83 | 2.12 | 26.77 | 53.74 |
| B-3 | 38 hr | 9.63 | 2.08 | 25.95 | 49.05 |
| B-4 | 62 hr | 9.5 | 2.05 | 25.34 | 44.96 |
| C-1 | 0 hr | 10 | 2.09 | 26.52 | 55.01 |
| C-2 | 14 hr | 9.99 | 2.08 | 26.45 | 54.83 |
| C-3 | 38 hr | 9.9 | 2.07 | 25.94 | 54.24 |
| C-4 | 62 hr | 9.76 | 2.04 | 25.91 | 53.47 |
| C-5 | 158 hr | 9.36 | 1.96 | 24.31 | 42.93 |
| D-1 | 0 hr | 10.17 | 2.03 | 26.03 | 54.75 |
| D-2 | 14 hr | 10.22 | 2.04 | 25.84 | 55.01 |
| D-3 | 38 hr | 10.08 | 2.01 | 25.72 | 54.06 |
| D-4 | 62 hr | 9.91 | 1.98 | 25.05 | 53.27 |
| D-5 | 158 hr | 9.62 | 1.92 | 24.26 | 51.48 |
| D-6 | 212 hr | 9.23 | 1.99 | 25.13 | 50.44 |
| E-1 | 0 hr | 10.45 | 1.94 | 24.71 | 54.03 |
| E-2 | 14 hr | 10.38 | 1.93 | 24.6 | 53.72 |
| E-3 | 38 hr | 10.45 | 1.94 | 24.74 | 54.13 |
| E-4 | 62 hr | 10.24 | 1.9 | 24.57 | 52.93 |
| E-5 | 158 hr | 9.9 | 1.84 | 23.44 | 51.15 |
| E-6 | 212 hr | 9.16 | 1.91 | 24.32 | 50.19 |

Collectively this data shows that increasing the proportion of crude COFA in the distilled/crude mixtures offers more protection to COFA losses from oxidation.

Example 2

Effect of Oxidized COFA on an Isobutanologen

The negative effect of oxidized COFA was shown by the reduction on glucose uptake rate observed when a culture of an isobutanologen was exposed to a secondary liquid phase of oxidized COFA. The oxidized COFA was prepared ex situ by exposing distilled COFA (i.e., COFA without antioxidant capacity) to a stream of breathing air for a period of time such that the peroxide value increased from less than 10 to about 100 meq/kg. A portion of this material was further processed by heating under $N_2$ atmosphere to about 80° C. and so the peroxide value was reduced to less than 10 meg/kg and the intermediary peroxides were converted to secondary oxidation products. These two materials are referred to as primary and secondary oxidized COFA. The culture of the isobutanologen with residual glucose present and negligible isobutanol or isobutanol side products was exposed to either primary or secondary oxidized COFA. The rate of glucose consumption of the isobutanologen in batch culture exposed to oxidized COFA was observed over a 48 hour period. The oxidized COFA (100 meq/kg) reduced the glucose consumption rate to zero. The experiment was repeated at two different initial cell counts and demonstrated that the oxidized COFA affected the specific growth rate as well as the specific glucose consumption rate.

Example 3

Effect of Range of Oxidized COFA on an Isobutanologen

Prophetic

In order to determine the effect of a range of COFA oxidation on glucose consumption rate and growth rate of the recombinant microorganism, the oxidized COFA is blended with virgin COFA (i.e., COFA with a peroxide value of less than 10 meq/kg) to give a COFA peroxide value or putative secondary oxidation product range of 10 to 100 meq/kg. The rate of glucose consumption of the isobutanologen in batch culture exposed to the COFA blends is observed over a 48 hour period.

Example 4

Maintaining or Providing an Effective Amount of Antioxidants or Antioxidant-Like Compounds in COFA Prophetic
General Methods
Fermentation Protocol.

900 µL of a −80° C. frozen vial lot of an isobutanologen yeast strain comprising an engineered butanol biosynthetic pathway (Optical density (OD) approximately 2.0, SEG media, 30% glycerol) is slowly thawed on ice/water and added to 150 mL of DM in a 2 liter (L) baffled shake flask (Defined medium (DM) is shown in Table 4). The culture is incubated in the presence of breathing air at 30° C. and 250 rpm for 24 hours after which the culture is centrifuged at 9000 rcf for 15 minutes and the recovered yeast cell pellet is resuspended in 150 mL corn mash. Corn mash is prepared using 30% ground dry corn solids (DCS) in city water with addition of Spezyme Fred-L in batch at 85° C. for 90 minutes. This liquefact is then autoclaved at 2 bar for 15 minutes. After cooling to room temperature, 2 g/L of urea, 35 g/L glucose, 10% v/v 1M MES buffer and 5 g/L ethanol is added and the mash is aliquoted and frozen at −20° C. until required. The yeast inoculated mash is added to a 2 L baffled flask and a further 150-450 mL of corn oil fatty acid (COFA) is added and the mixture is incubated in the presence of breathing air at 30° C. and 250 rpm for 48 hours. The aqueous and organic phases are sampled at 0 hours, 6 hours, 24 hours, 30 hours and 48 hours and at least analyzed for isobutanol and glucose. The yield of isobutanol on consumed glucose and the volumetric isobutanol production rate is calculated.

TABLE 4

| Defined Media (DM) | |
| --- | --- |
| Seed Flask Medium Ingredient | Total Needed |
| Yeast nitrogen base w/o AA (Difco) | 6.7 g/L |
| Sigma Y2001 yeast dropout mix | 2.8 g/L |
| 10 g/L leucine solution | 20.0 ml/L |
| 10 g/L tryptophan solution | 4.0 ml/L |
| Yeast Extract (Difco) | 2.0 g/L |
| Peptone (Bacto) | 4.0 g/L |
| MES Buffer | 38.4 g/L |
| Dextrose - Anhydrous | 10.0 g/L |
| Ethanol | 6.3 mL/L |

Corn Oil Fatty Acids (COFA).

The source of COFA is either crude or distilled. Crude COFA is prepared by alkaline hydrolysis of crude corn oil collected from the back-end of a corn-to-ethanol mill. The corn oil is exposed to alkali until the free acid content is greater than 95%. The material is water washed and brine dehydrated. The peroxide value (PV) is less than 1 meq/kg and the fatty acid (FA) composition is approximately: palmitic acid 12.2%; stearic acid 1.9%; oleic acid 26%; linoleic acid 57.7%; and linolenic acid 2%. Distilled COFA is purchased from Emery Oleochemicals. Distilled COFA is produced as the crude material and then boiled. The product is collected as a condensed product (thus essentially pure free fatty acids (FFA) without antioxidant or other naturally occurring lipids).

Experimental Results.

Three rounds of experiment are performed. In the first round there are two parallel experiments, (a) using crude COFA and (b) using distilled COFA. The protocol described above is serially used such that fresh mash/yeast (i.e., isobutanologen) is employed in each passage, but the COFA is recovered after each use, stripped of isobutanol and then redeployed. The recycling is continued until isobutanol production ceased. Because isobutanol accumulates in the COFA phase during each passage, it is stripped prior to subsequent reuse and this is carried out by 2 hours of $N_2$ sparging at 70° C. in a glass flask. In this way the isobutanol content at T=0 is approximately zero each time. A sample of COFA was taken for peroxide value (PV) and for fatty acid (FA) compositional analysis.

The cell performance, yield and rate, upon each reuse of COFA is measured. After 3-4 cycles of distilled COFA, growth yield and rate is expected to be reduced, whereas growth yield or rate is not expected to be reduced for crude COFA for greater than 10 cycles. The PV and FA composition are also measured. Antioxidative activity index of the extractant is also measured. A correlation between deterioration of cell performance and the extent of COFA oxidation is observed.

In the second round, the distilled COFA is used in each of three separate, but identical and parallel experiments. The recycling, as described above, is carried out in the experiments. In the first experiment, the system is left to deteriorate due to COFA oxidation. In the second and third experiments, the system is rescued by i) addition of a small feed (10% v/v) of fresh crude COFA at the critical passage number and ii) addition of casamino acids (approx. 3% w/w of the DCS) at each passage (including the first). Growth yield and rate are measured for the rescue experiments. The loss of cell performance due to COFA oxidation is observed in the experiment where the distilled COFA is not rescued with crude COFA or casamino acids. Supplementation of the system with a split of crude COFA or casamino acids is able to extend the utility of COFA.

Addition of casamino acids provides a simulation of protease release of amino acids from proteins already available in the corn mash, but not likely used. In the third round of experiments corn mash is dosed with a protease and the released free amino acids are measured. The protease is dosed at each recycle of COFA, and the experiment essentially repeated as described above. Release of free amino acids from mash correlates with the direct addition of casamino acids.

In each of the experiments described above, the fermentation media can be a minimal media such that the fermentation media is substantially reduced of or devoid of amino acids, particularly for experiments where the effect of casamino acids is to be determined. In these experiments, the fermentation media is substantially reduced or devoid of amino acids for both the control sample (i.e., the sample without added casamino acids) and the experimental sample (i.e., the sample with the added casamino acids).

Example 5

Identifying Oxidation of Extractant During Fermentation

Prophetic

To identify whether oxidation of the extractant has occurred during the fermentation process, several fermentation parameters are measured. Briefly, a recombinant microorganism comprising a butanol biosynthetic pathway is grown under culture conditions conducive for the fermentation process wherein extractant is mixed in with the fermentation media. The extractant is stripped of butanol and recycled as described above. At each recycle of the extractant, the oxidation state of the extractant is determined (e.g., by determining the antioxidative activity index using the Rancimat method, by measuring the loss of one or more components of the extractant, by measuring the peroxide, aldehyde, and/or ketone content of the extractant, or by measuring the presence of one or more antioxidant or antioxidant-like compounds of the extractant). Further, the metabolic parameters of the recombinant microorganism are measured during the fermentation after each recycle of extractant. Specifically, the metabolic parameters of the microorganism that are measured include, but are not limited to, the optical density (OD), pH, respiratory quotient, fermentable carbon substrate utilization, $CO_2$ production, and butanol production. Other metabolic parameters known in the art can be measured as well. A correlation between the oxidation state of the extractant introduced into the fermentation medium and each metabolic parameter of the recombinant microorganism during the fermentation process is determined.

Alternatively, extractant with known oxidation states (e.g., known peroxide levels) are introduced to the fermentation media and the recombinant microorganism comprising a butanol biosynthetic pathway is grown under culture conditions conducive for the fermentation process. During the fermentation process, the metabolic parameters of the recombinant microorganism are measured as described above, and a correlation between the known oxidation states of the extractant and each metabolic parameter measured is determined and is shown in Table 5.

TABLE 5

The effect of oxidation state on metabolic parameters of recombinant microorganism.

| Peroxide level of extractant | OD | pH | Resp. quotient | Carbon substrate utilization | $CO_2$ Prod. | Butanol Prod. |
|---|---|---|---|---|---|---|
| 0 meq/kg | | | | | | |
| 10 meq/kg | | | | | | |
| 25 meq/kg | | | | | | |
| 50 meq/kg | | | | | | |
| 75 meq/kg | | | | | | |
| 100 meq/kg | | | | | | |

Example 6

Supplementing Extractant with Antioxidants and the Resulting Effect of Supplementation on Butanol Rate, Titer, Yield, and Growth of the Microorganism Prophetic To determine whether supplementation of the extractant with antioxidants or antioxidant-like compounds has an effect on butanol production rate, titer, yield, and growth, the extractant is supplemented with increasing levels of various antioxidants or antioxidant-like compounds and butanol rate, titer, yield, and the growth of the recombinant microorganism are measured during the fermentation process.

Briefly, a recombinant microorganism comprising a butanol biosynthetic pathway is grown in culture conditions conducive for the fermentation process as carried out by one skilled in the art. To test whether supplementation of the extractant with antioxidants or antioxidant-like compounds affect butanol rate, titer, and yield of product alcohol, and growth of the microorganism, multiple samples of extractant comprising increasing amounts of antioxidants or antioxidant-like compounds are introduced in the fermentation process as shown in Table 6. Additionally, different types of antioxidants or antioxidant-like compounds are tested as shown in Table 7. After the fermentation process is complete, the butanol rate, titer, and yield are measured according to methods known in the art. The growth rate of the microorganism is also measured according to methods known in the art.

TABLE 6

The effect of increasing concentrations of antioxidant or antioxidant-like compounds on butanol rate, titer, yield, and growth of the recombinant microorganism.

| Antioxidant/ Antioxidant-Like Concentration | Butanol Production Rate | Butanol Titer | Butanol Yield | Microorganism Growth Rate |
|---|---|---|---|---|
| 0 | | | | |
| 1X | | | | |
| 10X | | | | |
| 100X | | | | |
| 1000X | | | | |

TABLE 7

The effect of type of antioxidant or antioxidant-like compound on butanol rate, titer, yield, and growth of the recombinant microorganism.

| Antioxidant/ Antioxidant-Like Compound | Butanol Production Rate | Butanol Titer | Butanol Yield | Microorganism Growth Rate |
|---|---|---|---|---|
| Tocopherols | | | | |
| Amino Acids | | | | |
| Tocotrienols | | | | |
| Butylated hydroxyanisole (BHA) | | | | |
| Butylated hydroxytoluene (BHT) | | | | |
| Alkylated Phenols | | | | |
| Epigallocatechin gallate (EGCG) | | | | |
| Epigallocatechin (EGC) | | | | |
| Epicatechin gallate (ECG) | | | | |
| Gallic Acid | | | | |
| Carnosol | | | | |
| Carnosic Acid | | | | |
| Ursolic Acid | | | | |
| Tanshen I | | | | |
| Dihydrotanshinone | | | | |
| Tanshinone IIA | | | | |
| Tanshinone IIB | | | | |
| Danshenxinkun B | | | | |
| Immobilized Borohydrides | | | | |
| L-ascorbic acid 6-palmitate | | | | |
| Anthocyanidin | | | | |
| Anthocyanin | | | | |
| Ethoxyquin | | | | |
| Tertiary-butylhydroquinone (TBHQ) | | | | |
| Propyl gallate | | | | |

Example 7

Evaluation of Antioxidant Activity in COFA by the Oil Stability Index (OSI)

Sample Preparation

Antioxidants were added on a weight percent basis to quantities of Corn Oil Fatty Acids (CAS No. 8001-30-7) and allowed to dissolve. Samples were prepared with crude corn oil fatty acids (COFA) prepared as described above; and other samples were prepared using distilled COFA (Emery Oleochemicals), which did not contain natural antioxidants. Antioxidants gallic acid and L-ascorbic acid 6-palmitate were not soluble at the concentrations tested. COFA samples containing undissolved antioxidants were thoroughly mixed before withdrawing samples for analysis, to ensure the samples contained the specified weight percent of antioxidant.

Antioxidant Activity Evaluation

Figure 3:
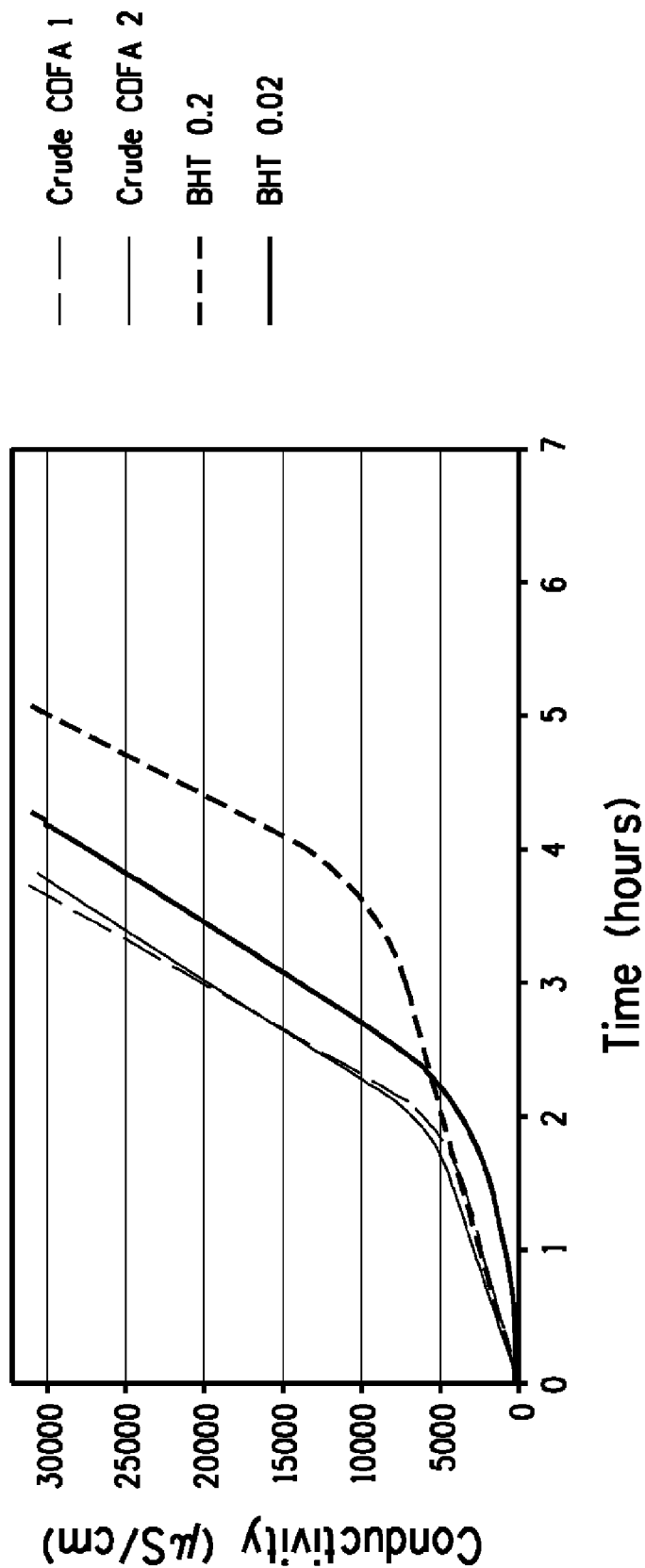
FIG. 3 shows a graph demonstrating the oxidative stability index at 110° C. for crude COFA and crude COFA plus different levels of BHT.

Crude and distilled COFA samples, with and without antioxidants, were evaluated using the Oxidative Stability Instrument from Omnion, Inc., Rockland, Mass., USA. Samples were run and the induction periods were determined according to AOCS method Cd 12b-92. All samples were tested at 110° C. Antioxidant activity was calculated as the ratio of the induction period of sample plus antioxidant to the induction period of plain crude or distilled COFA. Results are shown in Table 8. The effect of adding the antioxidant butylated hydroxytoluene (BHT) (Cat. No. W218405, Sigma Aldrich, Saint Louis, Mo., USA) on the induction period of crude COFA is shown in FIG. 3.

TABLE 8

Oxidative stability index at 110° C. for Crude and Distilled COFA supplemented with antioxidants

| COFA | Antioxidant | Dose (Wt %) | Sample (g) | OSI (hrs) | Activity Index |
|---|---|---|---|---|---|
| Distilled | | | | 0.1 | |
| 90:10 Distilled/Crude | | | | 0.5 | |
| Crude | | | | 5.06 | 5.45 |
| Crude | | | | 5.08 | 5.45 |
| Crude | | | | 5.0093 | 5.5 |
| Distilled | | | | 5.01 | 0.15 |
| Distilled | | | | 5.03 | 0.15 |
| Distilled | | | | 5.1077 | 0.1 |
| Distilled | a-Tocopherol | 0.2 | 5.11 | 0.35 | 2.63 |
| Distilled | a-Tocopherol | 1.1 | 5.09 | 0.15 | 1.13 |
| Distilled | a-Tocopherol | 2 | 5.12 | 0.15 | 1.13 |
| Distilled | BHT | 0.2 | 5.19 | 2.35 | 17.63 |
| Distilled | BHT | 1.1 | 5.07 | 7 | 52.50 |
| Distilled | BHT | 2 | 5.09 | 8.8 | 66.00 |
| Distilled | Mix Tocopherol | 0.2 | 5.0424 | 1.1 | 8.25 |
| Distilled | Mix Tocopherol | 2 | 5.0403 | 0.1 | 0.75 |
| Crude | | | 5.03 | 4.9 | |
| Crude | | | 5.02 | 4.4 | |

TABLE 8-continued

Oxidative stability index at 110° C. for Crude and Distilled COFA supplemented with antioxidants

| COFA | Antioxidant | Dose (Wt %) | Sample (g) | OSI (hrs) | Activity Index |
|---|---|---|---|---|---|
| Crude | a-Tocopherol | 0.217 | 5.15 | 5.05 | 1.09 |
| Crude | a-Tocopherol | | 5.11 | 6.4 | 1.38 |
| Crude | Gallic acid | 0.193 | 5.11 | 7.9 | 1.70 |
| Crude | Gallic acid | | 5.18 | 5.8 | 1.25 |
| Crude | Mix Tocopherol | 0.207 | 5.05 | 7.45 | 1.60 |
| Crude | Mix Tocopherol | | 5.08 | 9.75 | 2.10 |
| Crude | BHT | 0.205 | 5.14 | 11.3 | 2.43 |
| Crude | BHT | | 5.03 | 12.65 | 2.72 |
| Crude | | | 5.11 | 1.55 | |
| Crude | | | 5.14 | 1.3 | |
| Crude | BHT | 0.2020 | 5.12 | 3 | 2.11 |
| Crude | BHT | 0.2097 | 5.08 | 2.95 | 2.07 |
| Crude | Irganox 1330 | 0.2046 | 5.07 | 2.35 | 1.65 |
| Crude | Irganox 1135 | 0.2201 | 5.08 | 2.5 | 1.75 |
| Crude | Chimassorb 944 | 0.2062 | 5.07 | 2.35 | 1.65 |
| Crude | Ethoxyquin | 0.2074 | 5.06 | 0.95 | 0.67 |
| Crude | Phenothiazine | 0.2034 | 5.06 | 2.3 | 1.61 |
| Crude | TBHQ | 0.2082 | 5.09 | 3.7 | 2.60 |
| Crude | L-ascorbic acid 6-palmitate | 0.2045 | 5.19 | 26.4 | 18.53 |
| Crude | Guardian Chelox L | 0.2195 | 5.06 | 7.25 | 5.09 |
| Crude | | | 5.01 | 1.35 | |
| Crude | | | 5.02 | 1.25 | |
| Crude | TBHQ | 0.2000 | 5.01 | 3.65 | 2.81 |
| Crude | TBHQ | 0.0200 | 5.01 | 1.75 | 1.35 |
| Crude | L-ascorbic acid 6-palmitate | 0.2000 | 5.04 | 25.4 | 19.54 |
| Crude | L-ascorbic acid 6-palmitate | 0.0200 | 5.03 | 4.1 | 3.15 |
| Crude | Guardian Chelox L | 0.2000 | 5.02 | 6.4 | 4.92 |
| Crude | Guardian Chelox L | 0.0200 | 5 | 1.65 | 1.27 |
| Crude | | | 5.07 | 1.35 | |
| Crude | | | 5.12 | 1.25 | |
| Crude | | | 5.11 | 1.65 | |
| Crude | | | 5.01 | 1.45 | |
| Crude | | | 5.19 | 1.45 | |
| Crude | BHT | 0.1998 | 5.05 | 2.85 | 2.19 |
| Crude | BHT | 0.0200 | 5.14 | 1.85 | 1.42 |
| Crude | L-ascorbic acid 6-palmitate | 0.2000 | 4.99 | 29.8 | 22.92 |
| Crude | L-ascorbic acid 6-palmitate | 0.0100 | 5.01 | 10.05 | 7.73 |
| Crude | L-ascorbic acid 6-palmitate | 0.0020 | 5.13 | 5.45 | 4.19 |

Example 8

COFA Oxidation and Biocompatibility

Reaction Vessel Preparation

Three glass jacketed, 1 L cylindrical reaction vessels (Wilmad-LabGlass; Vineland, N.J.) were charged with 850 g of crude Corn Oil Fatty Acids (CAS No. 8001-30-7). The reaction vessel lid, 3 or 4 neck, was tightly sealed onto the reaction vessel. A 4 bladed glass stir shaft, polytetrafluoroethylene (PTFE) stirrer bearing, and a gas dispersion tube were installed into the reactor vessel and lid. A glass condenser was also installed onto the reactor using an offset adapter. Metal coupons (304 stainless steel, 1"×2") were placed at the bottom of the reactor. A glass stopper was installed into any remaining openings in the lid. The jacketed water supply and return lines were connected to a refrigerated/heated circulating bath (VWR; Radnor, Pa.), set to 30° C. The condenser cooling water in and water out lines were connected to a NesLab refrigerated/heated circulating bath (ThermoFisher Scientific; Waltham, Mass.), set to 15° C. The vent line transferred the sparged gas from the reaction system through a double gas bubbler, containing mineral oil, to the ventilation system. The antioxidant butylated hydroxytoluene (Cat. No. W218405, Sigma-Aldrich, Saint Louis, Mo.) was loaded into reactors 2 and 3 at concentrations of 0.2, and 0.8 wt. %, respectively. Nitrogen gas was sparged at a rate of 0.024 std. L/min and the stirring speed was maintained constant at 300 rpm. To ensure the antioxidant was fully dissolved, the reaction systems were left under nitrogen sparging for 68 hours.

COFA Oxidation

After nitrogen sparging, the gas was secured and the jacketed water supply circulating bath was set to 60° C. Compressed air was then sparged into the reactor vessel at a rate of 0.034 std. L/min, which marked time t=0 of the experiment. Samples were taken from reactors 1, 2, and 3 at 0, 6, 52, 124, 168, and 222 hours. Samples were purged with nitrogen and frozen in a −20° C. freezer. The samples were later thawed and aliquoted for biocompatibility analysis.

Biocompatibility

A 1 mL vial of an isobutanologen (approx. OD=1.0) was thawed and inoculated into 20 mL of SG30 media (glucose 30 g/L; yeast extract 2 g/L; yeast nitrogen base (YNB) 6.7 g/L; dropout 2 g/L; MES 30 g/L; pH titrated to 5.5 with KOH and filter sterilized) in a 125 mL vented flask and incubated for about 24 hr at 30° C. and 240 rpm shaking. The culture was passaged into 500 mL in a 2 L flask and incubated for a further period at the same conditions until the OD was approximately 2.0. The cells where recovered by centrifugation at 7000 rpm for 10 minutes at RT and the supernatant was discarded. The cell pellet was resuspended into fresh SG30 to an OD of 1.0 and 20 mL of this resuspension was placed into a flask (unvented). The extractant to be evaluated was added (10 mL) and sterile nitrogen ($N_2$) gas was filled into the headspace of the flask. The flask was then capped and incubated as indicated above. Samples of the biphasic system were taken from the flask periodically and centrifuged at 15000 rpm such that an aqueous phase devoid of extractant and cells was obtained. The glucose concentration in this phase was determined by YSI or liquid chromatography (LC) methods, and the rate of glucose consumption was determined over time as a measurement of fermentation activity.

The contents of reactor 1, which did not contain additional BHT, demonstrated a loss in biocompatibility in the samples taken at 124 and 168 hours into the oxidation study (FIG. 4A). Reactors 2 and 3, which contained 0.2 and 0.8 wt. % BHT, respectively, continued to demonstrate biocompatibility in all samples (FIGS. 4B and 4C). Control samples were taken from the bulk 5 gallon drum of COFA, from which all three reactors were initially filled.

Example 9

COFA, BHT, and Biocompatibility

Seed Flask Growth

An isobutanologen was grown in defined medium (Difco™ Yeast Nitrogen Base without amino acids 6.7 g/L, ForMedium™ Synthetic Complete Drop-out (Kaiser) Mix-HIS, -Ura 3.7 g/L, MES Buffer 19.5 g/L, Dextrose 30 g/L). The medium's pH was adjusted to 5.8-6.2 using sodium hydroxide. The culture started in a seed flask (500 mL of this defined medium in 2 L, baffled, vented shake flask) by adding part of a thawed, vial to the flask with defined medium, at 29-31° C., in an incubator rotating at 260-300 rpm, grown to a final biomass concentration of 0.68 optical density (600 nanometer wavelength).

Biocompatibility Flask Test

The seed flask culture was sub-cultured into defined medium (40 g/L dextrose) with a starting optical density of 0.05 units (600 nanometer wavelength). 20 mL of this subculture was added to a 250 mL Erlenmeyer flask. Separately, butylated hydroxytoluene (BHT; Sigma Aldrich) was dissolved into COFA at various concentrations (0, 0.2, 0.4, 0.8, and 5.0 wt %). 20 mL of COFA containing BHT was added to the 250 mL Erlenmeyer flask containing the subculture material. A control flask was prepared in the same manner using COFA containing no BHT. The flasks were then incubated in an incubator rotating at 260 rpm. Samples were removed during the culture and analyzed for cell count and glucose concentration utilizing methods disclosed herein. COFA with 5% BHT supported growth of the isobutanologen as indicated in Tables 9 and 10.

TABLE 9

COFA, BHT, and cell growth

| | | Cell Count ($\times 10^7$ cells/mL) over time (hr) | | | | | |
|---|---|---|---|---|---|---|---|
| Sample | BHT (wt %) | 0 | 6.7 | 23.3 | 26.9 | 30.0 | 32.8 |
| 1 | 0.0 | 0.098 | 0.243 | 2.413 | ND | 4.40 | 4.60 |
| 2 | 0.0 | 0.100 | 0.198 | 1.713 | ND | 2.45 | 4.65 |
| 3 | 0.2 | 0.048 | 0.200 | 1.363 | ND | 3.68 | 5.00 |
| 4 | 0.4 | 0.038 | 0.165 | 1.775 | ND | 2.88 | 5.08 |
| 5 | 0.8 | 0.093 | 0.203 | 1.238 | ND | 4.10 | 4.70 |
| 6 | 5.0 | 0.085 | 0.123 | 2.550 | ND | 2.55 | 5.05 |

TABLE 10

COFA, BHT, and glucose concentration

| | | Glucose concentration (g/L) over time (hr) | | | | | |
|---|---|---|---|---|---|---|---|
| Sample | BHT (wt %) | 0 | 6.7 | 23.3 | 26.9 | 30.0 | 32.8 |
| 1 | 0.0 | 38.5 | 39.5 | 34.5 | 30.0 | 24.6 | 18.9 |
| 2 | 0.0 | 39.0 | 38.5 | 33.9 | 30.0 | 25.5 | 19.2 |
| 3 | 0.2 | 39.0 | 39.0 | 32.4 | 28.8 | 24.3 | 18.3 |
| 4 | 0.4 | 38.0 | 39.0 | 33.3 | 29.7 | 24.6 | 18.3 |
| 5 | 0.8 | 38.5 | 39.0 | 33.3 | 29.4 | 24.6 | 18.3 |
| 6 | 5.0 | 39.0 | 38.5 | 34.2 | 28.8 | 23.7 | 18.3 |

What is claimed:

1. A process comprising:
   (a) providing a fermentation medium comprising a fermentable carbon source, a recombinant microorganism comprising an engineered butanol biosynthetic pathway, and butanol;
   (b) contacting said fermentation medium with an extractant composition comprising an effective amount of antioxidant, whereby at least a portion of the butanol in the fermentation medium partitions into the extractant;
   (c) recovering at least a portion of the butanol and extractant composition from the fermentation medium;
   (d) recycling the extractant composition recovered in (c) one or more times to the fermentation medium; and
   (e) adjusting the effective amount of antioxidant in the extractant composition whereby the rate of oxidation of recycled extractant composition is substantially reduced such that the extractant composition may be recycled as provided in step (d) for at least ten recycles.

2. The process of claim 1, wherein adjusting the effective amount of antioxidant of the extractant composition comprises supplementing the extractant composition with one or more antioxidants.

3. The process of claim 2, wherein the one or more antioxidants are selected from the group consisting of tocopherols, tocotrienols, amino acids, butylated hydroxyanisole (BHA), butylated hydroxytoluene (BHT), other alkylated phenols, epigallocatechin gallate (EGCG), epigallocatechin (EGC), epicatechin gallate (ECG), gallic acid, carnosol, carnosic acid, ursolic acid, tanshen I, dihydrotanshinone, tanshinone IIA, tanshinone IIB, danshenxinkun B, peroxidase enzymes, and immobilized borohydrides.

4. The process of claim 3, wherein the one or more antioxidants are tocopherols.

5. The process of claim 1, wherein the fermentable carbon source is provided by processing biomass.

6. The process of claim 5, wherein the biomass is processed further by addition of a protease to the biomass, whereby addition of the protease releases free amino acids from the biomass.

7. The process of claim 6, wherein the protease is deactivated at a temperature of at least about 85° C.

8. The process of claim 1, wherein the extractant composition comprising an effective amount of antioxidant has an antioxidative activity index of at least 1.1.

9. The process of any one of claims 1-8, wherein the extractant is selected from the group consisting of corn oil fatty acid (COFA), soy oil fatty acid (SOFA), castor oil fatty acid, oleyl alcohol, COFA based fatty acid methyl esters (FAME), SOFA based FAME, fatty acid butyl esters (FABE), and mixtures thereof.

10. A process comprising:
   (a) providing a fermentation medium comprising a fermentable carbon source, a recombinant microorganism comprising an engineered butanol biosynthetic pathway, and butanol, wherein the fermentable carbon source is provided by processing biomass;
(b) contacting said fermentation medium with an extractant composition, whereby the extractant composition does not comprise an effective amount of antioxidant or antioxidant-like compound, and whereby at least a portion of the butanol in the fermentation medium partitions into the extractant;
(c) adjusting the amount of antioxidant or antioxidant-like compound in the extractant composition by further processing the biomass with a protease, whereby the protease stimulates the release of amino acids from the biomass and whereby the amino acids provide the extractant composition with an effective amount of antioxidant or antioxidant-like compound;
(d) recovering at least a portion of the butanol and extractant composition from the fermentation medium;
(e) recycling the extractant composition recovered in (d) one or more times to the fermentation medium; and
(f) adjusting the effective amount of antioxidant or antioxidant-like compound in the extractant composition whereby the rate of oxidation of recycled extractant composition is substantially reduced such that the extractant composition may be recycled as provided in step (e) for at least ten recycles.

11. The process of claim 10, wherein the protease is deactivated at a temperature of at least about 85° C.

12. The process of claim 10 or 11, wherein the extractant is selected from the group consisting of corn oil fatty acid (COFA), soy oil fatty acid (SOFA), castor oil fatty acid, oleyl alcohol, COFA based fatty acid methyl esters (FAME), SOFA based FAME, fatty acid butyl esters (FABE), and mixtures thereof.

13. A process comprising:
(a) providing a fermentation medium comprising a fermentable carbon source, a recombinant microorganism comprising an engineered butanol biosynthetic pathway; and butanol;
(b) contacting said fermentation medium with an extractant composition comprising an effective amount of antioxidant, whereby at least a portion of the butanol in the fermentation medium partitions into the extractant;
(c) recovering at least a portion of the butanol and extractant composition from the fermentation medium;
(d) adding antioxidants to the extractant composition recovered in (c); and
(e) recycling the extractant composition of step (d) one or more times in the fermentation medium.

14. A biphasic composition comprising:
(a) a first phase comprising fermentation medium comprising a fermentable carbon source, a recombinant microorganism comprising an engineered biosynthetic pathway for producing a product alcohol, and a product alcohol; and
(b) a second phase comprising an extractant composition comprising an effective amount of antioxidant, product alcohol and free fatty acids;
wherein the free fatty acids and antioxidant are derived from the fermentable carbon source.

15. The biphasic composition of claim 14, wherein the engineered biosynthetic pathway is a butanol biosynthetic pathway and the product alcohol is butanol.

16. A method for maintaining the oxidative state of an extractant composition during a butanol fermentation process comprising:

(a) providing a fermentation medium comprising a fermentable carbon source, a recombinant microorganism comprising an engineered butanol biosynthetic pathway; and butanol;
(b) contacting said fermentation medium with an extractant composition comprising an effective amount of antioxidant or antioxidant-like compound, whereby at least a portion of the butanol in the fermentation medium partitions into the extractant;
(c) recovering at least a portion of the butanol and extractant composition from the fermentation medium;
(d) monitoring one or more of the effective rate, titer, yield of butanol production or the growth of the recombinant microorganism during fermentation;
(e) supplementing the extractant composition with antioxidant following step (d) when said monitoring indicates a butanol toxicity to the recombinant microorganism.

17. A method for optimizing extraction of butanol from butanol fermentation comprising:
(a) providing a fermentation medium comprising a fermentable carbon source, a recombinant microorganism comprising an engineered butanol biosynthetic pathway; and butanol;
(b) providing an extractant composition comprising an effective amount of antioxidant or antioxidant-like compound, butanol and free fatty acids, wherein the antioxidant is produced by the recombinant microorganism during fermentation;
(c) contacting the fermentation medium of (a) with the extractant composition of (b) whereby the butanol partitions into the extractant composition and is distilled from the extractant.

18. The method of claim 17 further comprising recycling the extractant composition of (c) after the butanol is distilled.

19. A method for improving the yield of an isobutanol fermentation comprising:
(a) providing a fermentation medium comprising a fermentable carbon source, a recombinant microorganism comprising an engineered butanol biosynthetic pathway; and butanol;
(b) providing an extractant composition comprising an effective amount of antioxidant or antioxidant-like compound, butanol and free fatty acids,
(c) contacting the fermentation medium of (a) with the extractant composition of (b) whereby butanol partitions into the extractant composition;
wherein the yield of isobutanol is improved as compared to yield of isobutanol in the absence of the antioxidant.

20. A method for improving the titer of isobutanol produced during fermentation comprising:
(a) providing a fermentation medium comprising a fermentable carbon source, a recombinant microorganism comprising an engineered butanol biosynthetic pathway; and butanol;
(b) providing an extractant composition comprising an effective amount of antioxidant or antioxidant-like compound, butanol and free fatty acids,
(c) contacting the fermentation medium of (a) with the extractant composition of (b) whereby butanol partitions into the extractant composition;
wherein the titer of isobutanol production is improved as compared to titer of isobutanol production in the absence of the antioxidant.

21. A method for improving the rate of an isobutanol production during fermentation comprising:

(a) providing a fermentation medium comprising a fermentable carbon source, a recombinant microorganism comprising an engineered butanol biosynthetic pathway; and butanol;

(b) providing an extractant composition comprising an effective amount of antioxidant or antioxidant-like compound, butanol and free fatty acids, (c) contacting the fermentation medium of (a) with the extractant composition of (b) whereby the butanol partitions into the extractant composition, wherein the rate of isobutanol production is improved as compared to rate of isobutanol production in the absence of the antioxidant.

22. A process comprising:

(a) providing a fermentation medium comprising a fermentable carbon source, a recombinant microorganism comprising an engineered butanol biosynthetic pathway, and butanol;

(b) contacting said fermentation medium with an extractant composition comprising an effective amount of antioxidant or antioxidant-like compound, whereby at least a portion of the butanol in the fermentation medium partitions into the extractant;

(c) recovering at least a portion of the butanol and extractant composition from the fermentation medium;

(d) recycling the extractant composition recovered in (c) one or more times to the fermentation medium; and (e) adjusting the effective amount of antioxidant or antioxidant-like compound in the extractant composition whereby the effect of oxidation products of recycled extractant composition is substantially reduced such that the extractant composition may be recycled as provided in step (d) for at least ten recycles.

* * * * *